(12) United States Patent  (10) Patent No.: US 8,956,405 B2
Wang et al.  (45) Date of Patent: Feb. 17, 2015

(54) COLLAPSIBLE CAGED-BALL PROSTHETIC VALVE FOR TRANSCATHETER DELIVERY AND METHOD OF USE

(71) Applicant: Boston Scientific Scimed, Inc., Maple Grove, MN (US)

(72) Inventors: Huisun Wang, Maple Grove, MN (US); Pu Zhou, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 85 days.

(21) Appl. No.: 13/909,593

(22) Filed: Jun. 4, 2013

(65) Prior Publication Data

US 2014/0018935 A1    Jan. 16, 2014

Related U.S. Application Data

(60) Provisional application No. 61/671,210, filed on Jul. 13, 2012.

(51) Int. Cl.
*A61F 2/24* (2006.01)
*A61F 2/06* (2013.01)

(52) U.S. Cl.
CPC ............... *A61F 2/06* (2013.01); *A61F 2/2409* (2013.01); *A61F 2/2424* (2013.01); *A61F 2/2436* (2013.01); *A61F 2250/0003* (2013.01)
USPC .......... 623/2.35; 623/2.1; 623/2.14; 623/2.34

(58) Field of Classification Search
CPC ............................. A61F 2/2412; A61F 2/2418
USPC .................................. 623/1.24–1.26, 2.1–2.19
See application file for complete search history.

(56) References Cited

U.S. PATENT DOCUMENTS

| | | |
|---|---|---|
| 3,263,239 A | 8/1966 | Edwards et al. |
| 3,723,996 A | 4/1973 | Raible et al. |
| 4,922,905 A | 5/1990 | Strecker |
| 5,332,402 A | 7/1994 | Teitelbaum |
| 5,397,351 A | 3/1995 | Pavcnik et al. |
| 5,469,868 A | 11/1995 | Reger |
| 5,697,972 A | 12/1997 | Kim et al. |
| 6,245,103 B1 | 6/2001 | Stinson |
| 7,244,242 B2 | 7/2007 | Freyman |
| 7,462,192 B2 | 12/2008 | Norton et al. |
| 7,655,039 B2 | 2/2010 | Leanna et al. |
| 8,151,682 B2 | 4/2012 | Lilburn et al. |
| 2004/0210307 A1 | 10/2004 | Khairkhahan |
| 2005/0182483 A1 | 8/2005 | Osborne et al. |
| 2007/0078509 A1* | 4/2007 | Lotfy ............................ 623/1.24 |
| 2007/0168024 A1* | 7/2007 | Khairkhahan ............... 623/2.18 |

FOREIGN PATENT DOCUMENTS

| | | |
|---|---|---|
| GB | 2405919 | 3/2005 |
| GB | 2423132 | 8/2006 |

* cited by examiner

*Primary Examiner* — Jason-Dennis Stewart
(74) *Attorney, Agent, or Firm* — Vidas, Arrett & Steinkraus, P.A.

(57) ABSTRACT

A valve that includes an expandable valve body defining a lumen and a longitudinally moveable obstructer retained within the lumen of the valve body between the proximal and distal ends of the valve when the valve is in an expanded configuration. The valve, in the collapsed configuration, is delivered to a native valve site by a catheter where the valve body is expanded to anchor the valve at the valve annulus and the collapsed obstructer is subsequently expanded so that the valve is in the expanded configuration.

18 Claims, 14 Drawing Sheets

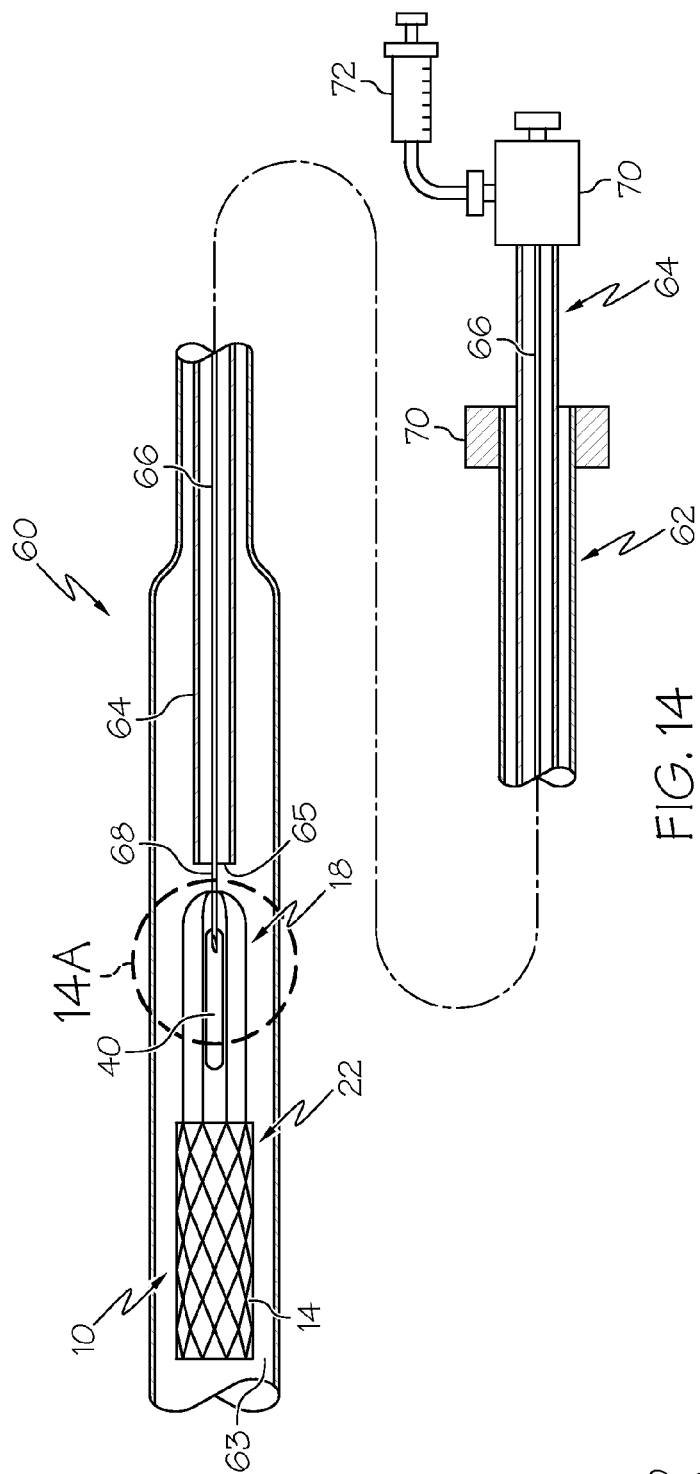
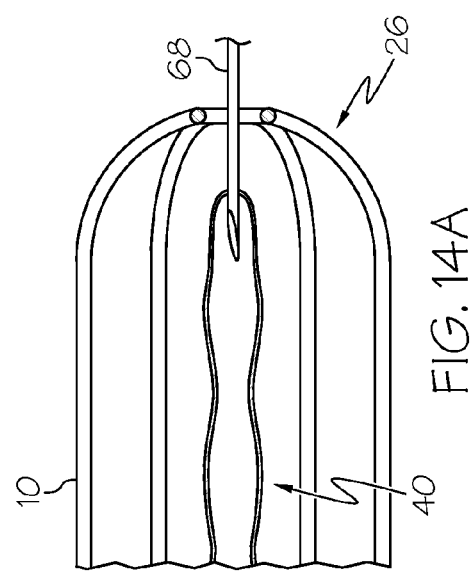
FIG. 14
FIG. 14A

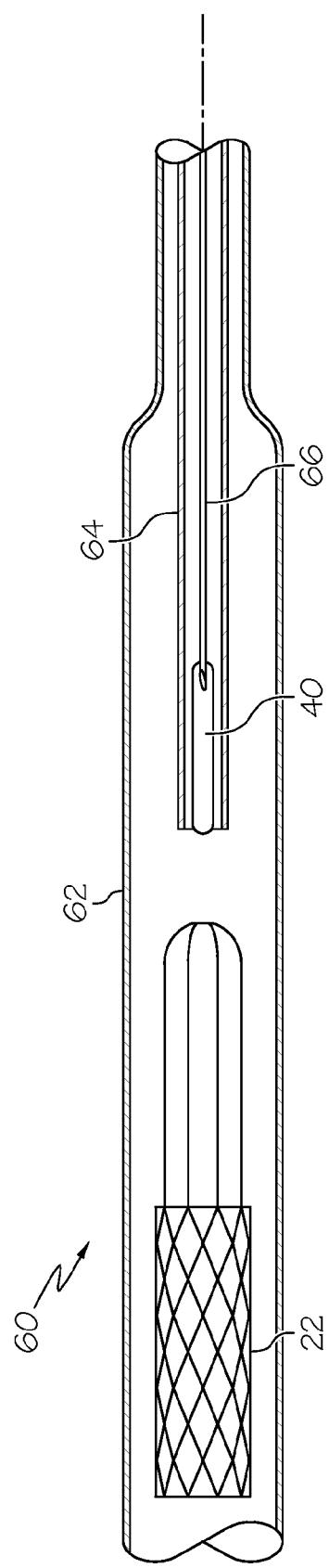
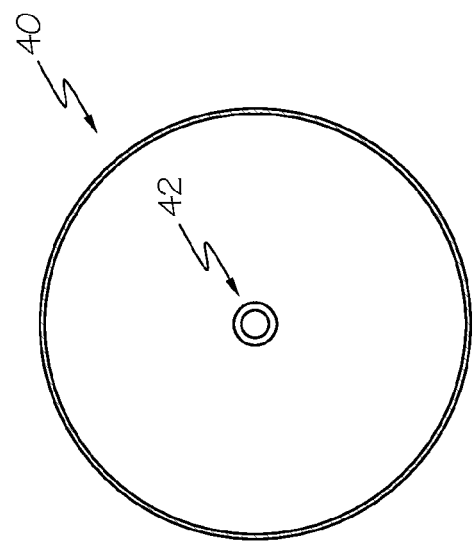

COLLAPSIBLE CAGED-BALL PROSTHETIC VALVE FOR TRANSCATHETER DELIVERY AND METHOD OF USE

CROSS-REFERENCE TO RELATED APPLICATIONS

This application claims priority to U.S. Patent Provisional Application No. 61/671,210, filed Jul. 13, 2012, the entire contents of which are hereby incorporated herein by reference.

STATEMENT REGARDING FEDERALLY SPONSORED RESEARCH

Not Applicable

BACKGROUND OF THE INVENTION

Valve replacement may be indicated when there is a narrowing of the native valve, commonly referred to as stenosis, or when the native valve leaks or regurgitates. Examples of valves that may be replaced include heart valves and venous valves. Valve replacement is used to repair or replace a diseased valve. To replace a heart valve, one method is open heart surgery. Another method to replace a heart valve, typically an aortic valve, is transcatheter aortic valve implantation (TAVI), developed to treat high-risk or inoperable severe aortic stenosis patients, which is known to have a poor prognosis clinically. Currently, TAVI is a fast growing procedure, with more than 20,000 patients treated worldwide. It has been recommended as an alternative strategy for patients in high-risk surgical groups. However, one of the technical challenges of TAVI is to reduce the delivery profile and increase the durability of the valve.

One type of prosthetic valve used for open heart surgery is a caged ball type heart valve which utilizes a metal cage to house a silicone elastomer ball and is sutured into place. An example of such a caged ball valve is the "Starr-Edwards" valve manufactured by Edwards Lifescience. When the caged ball valve is implanted as a replacement for a heart valve and blood pressure in the chamber of the heart exceeds the pressure on the outside of the chamber, the ball is pushed forward against the cage end and allows blood to flow through the valve. At the completion of the heart's contraction, the pressure inside the chamber drops and is lower than beyond the valve, so the ball moves back against the base of the valve forming a seal that prevents blood from flowing through the valve.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

The valves disclosed herein are embodiments of a new collapsible valve which can improve the valve durability and reduce the delivery profile. As discussed herein the valves are a stent based system with a ball or obstructer and are delivered by a delivery system through a blood vessel.

In some embodiments, the distal end region of the valve includes three or more arms joined at the distal end to form the distal end of the ball cage, where the ball movement is confined inside the cage. In at least one embodiment, the ball is either located inside the ball cage during delivery or it is pushed inside the ball cage after the stent is expanded at the valve base.

In at least one embodiment, the ball is a balloon that has a rubber injection outlet with a pre-loaded needle. Once the balloon is inside the cage, silicone liquid is injected into the balloon to inflate the balloon into a ball with a desired diameter and the needle is removed. When the valve embodiments disclosed herein are implanted, the ball will move back and forth within the valve due to blood flow pressure.

In at least one embodiment, a valve that is collapsible for delivery to a desired location within a body comprises a collapsible valve body and a longitudinally moveable collapsible obstructer positioned within the valve body. In some embodiments, the obstructer is expandable.

These and other embodiments which characterize the invention are pointed out with particularity in the claims annexed hereto and forming a part hereof. However, for further understanding of the invention reference can be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

FIGS. 14-15 are views of a delivery system with a valve.

FIG. 16 is an end view of the obstructer of the valves of FIGS. 1-8.

DETAILED DESCRIPTION OF THE INVENTION

Figure 1:
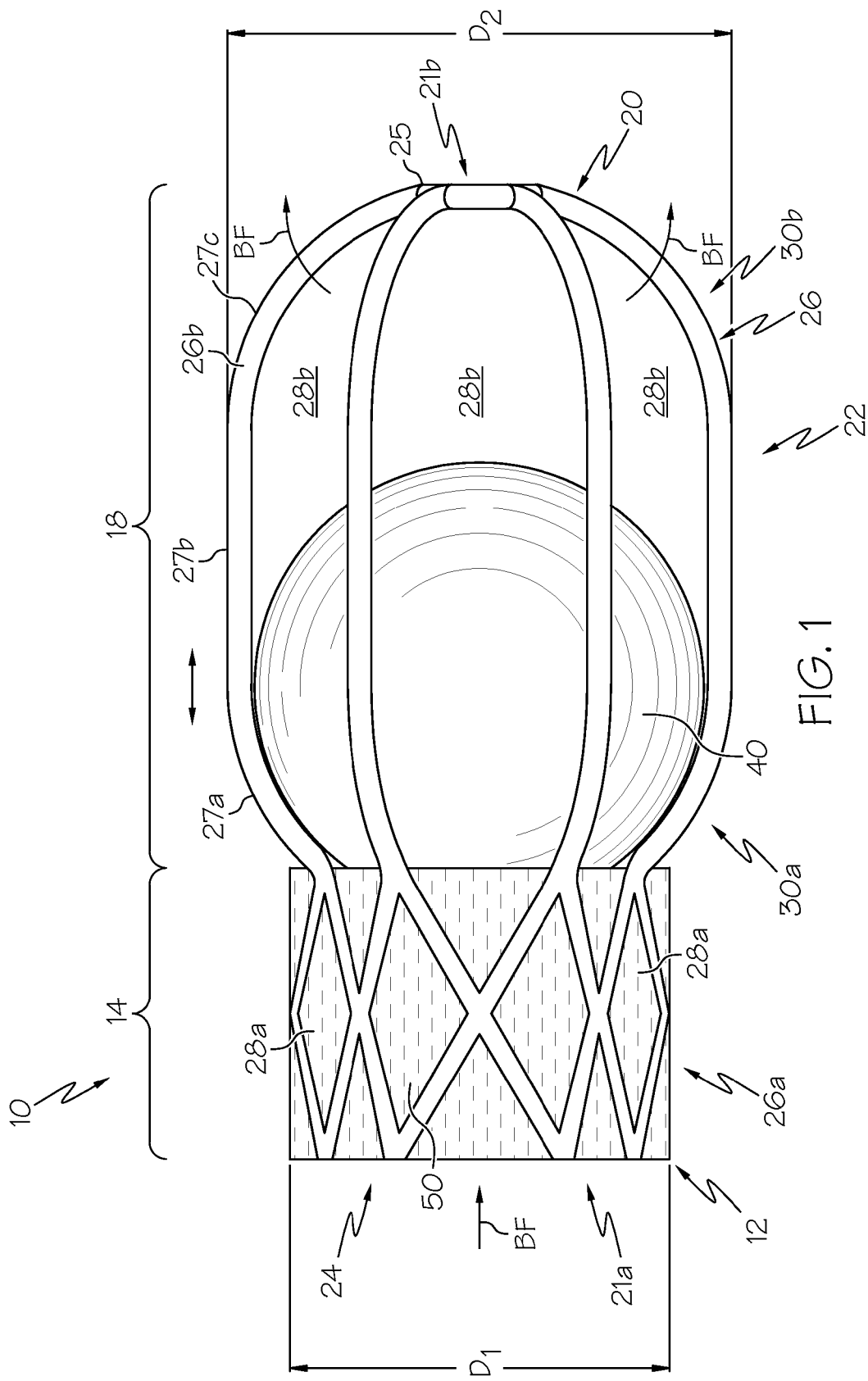
FIGS. 1-8 show valves comprising a stent and an obstructer.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

A. The Valve and Methods of Making the Valve

As shown in the figures, the valve 10 includes lumen 24, a proximal end 12, a distal end 20, a valve body 22, and an obstructer 40. As can be seen in FIGS. 1-8, the valve body 22 includes at least two regions 14, 16, 18, 30. As used in this application, the "proximal end" 12 and the "distal end" 20 of the valve 10 are determined relative to the flow of blood (BF) through the valve 10, with blood flow entering the valve 10 at the proximal end 12 and the distal end 20 being the other end of the valve 10. Since the valve body 22 extends the entire length of the valve 10, references to the proximal end 12, the proximal end region 14, the middle region 16, the distal end region 18, and the distal end 20, are applicable to both the valve 10 and the valve body 22. In at least one embodiment, the valve 10 is configured to contain the expanded obstructer 40 within the lumen 24. As used herein a "region" or "section" used in reference to the valve 10 or valve body 22 has a longitudinal length and extends around the entire circumference of the valve 10 or valve body 22.

In some embodiments, the valve body 22, and thus the valve 10, is tubular. In at least one embodiment, the valve body 22 defines the valve lumen 24 and is made of a plurality of elements 26. Each element 26 has a width, a length, thickness and a cross-sectional shape such as, but not limited to, round, rectangular, or square. FIGS. 1-8 show some non-limiting configurations for the elements 26.

In at least one embodiment, the valve 10 has a collapsed configuration, a partially expanded configuration, and an expanded configuration. As used herein, "expandable" or "expanded" refers to an increase in diameter as compared to the collapsed or unexpanded configuration or state and "collapsible" or "collapsed" refers to a decrease in diameter as compared to the expanded configuration or state. Therefore, the diameter of the valve body 22 in the expanded configuration or state is greater than the diameter of the valve body 22 in the collapsed configuration or state and the diameter of the valve body 22 in the collapsed configuration or state is less than the diameter of the valve body 22 in the expanded configuration or state. As used herein, "diameter" is the distance of a straight line extending between two points and does not indicate a particular shape.

As used herein when the valve 10 is in the "collapsed configuration," the valve body 22 and the obstructer 40 are both in a collapsed state; when the valve 10 is in the "partially expanded configuration," only the valve body 22 is in an expanded state while the obstructer 40 is in a collapsed state; and when the valve 10 is in the "expanded configuration," the valve body 22 is in an expanded state and the obstructer 40 is in an expanded state. For example, FIGS. 14-15 show a valve 10 in a collapsed configuration and FIGS. 1-8 show a valve 10 in an expanded configuration.

With regard to delivering the valve 10 to a site of implantation as discussed below in greater detail, the obstructer 40 may or may not be positioned within the lumen of the valve body 22 when the valve 10 is in the collapsed configuration and the obstructer 40 may or may not be positioned within the lumen of the valve body 22 when the valve 10 is in the partially expanded configuration.

In at least one embodiment, at least a portion of the valve body 22 is expandable. In some embodiments, at least a portion of the valve body 22 is self-expandable. In one embodiment, the entire valve body 22 is self-expandable. In other embodiments, at least a portion of the valve body 22 is balloon expandable. In one embodiment, the entire valve body 22 is balloon expandable. In still other embodiments, a portion of the valve body 22 is self-expandable and another portion of the valve body 22 is balloon expandable. For example, in some embodiments, the anchor region of the valve body is balloon expandable and the distal end region of the valve body is self-expandable.

Figure 2:
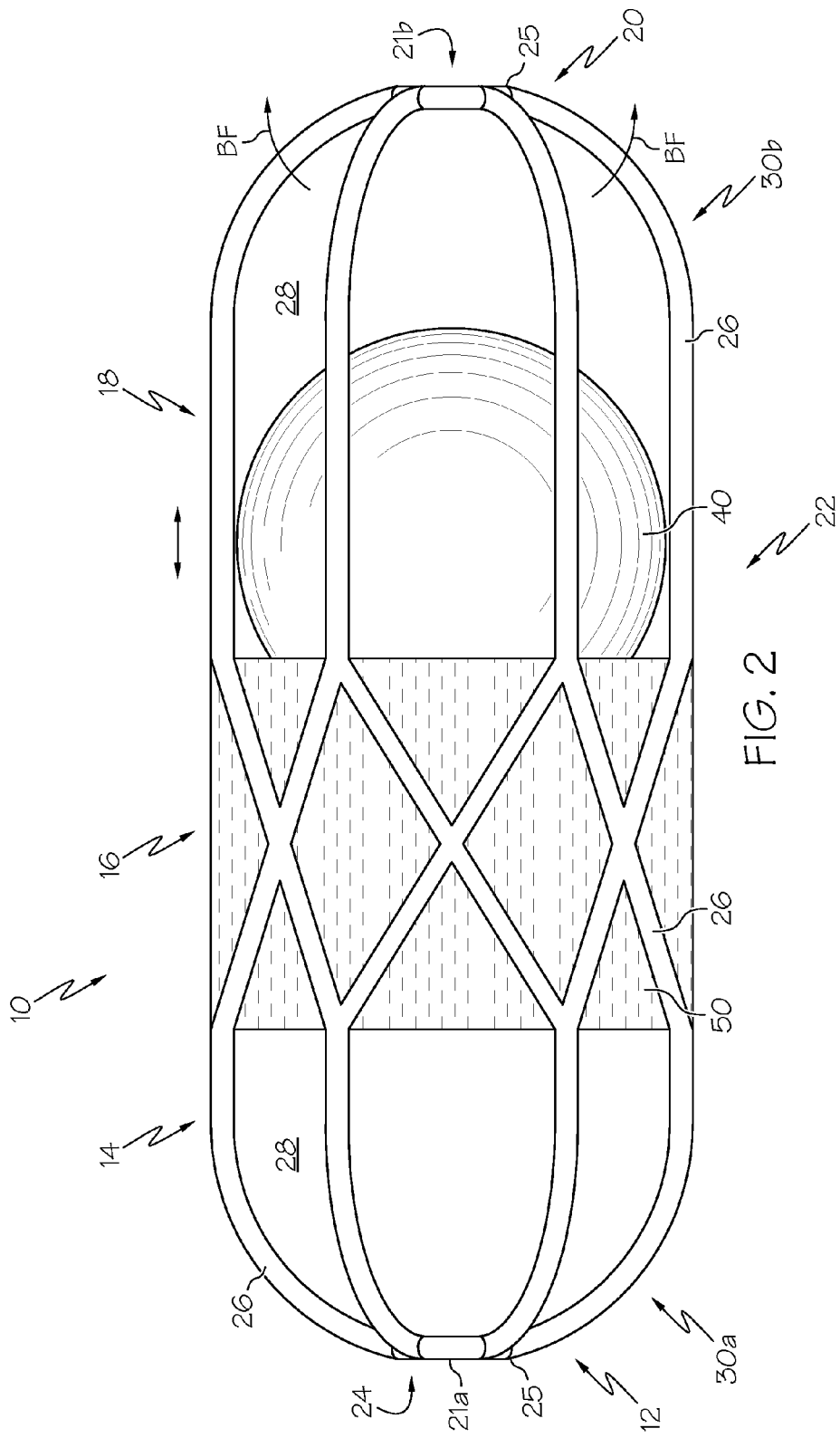
Figure 17:
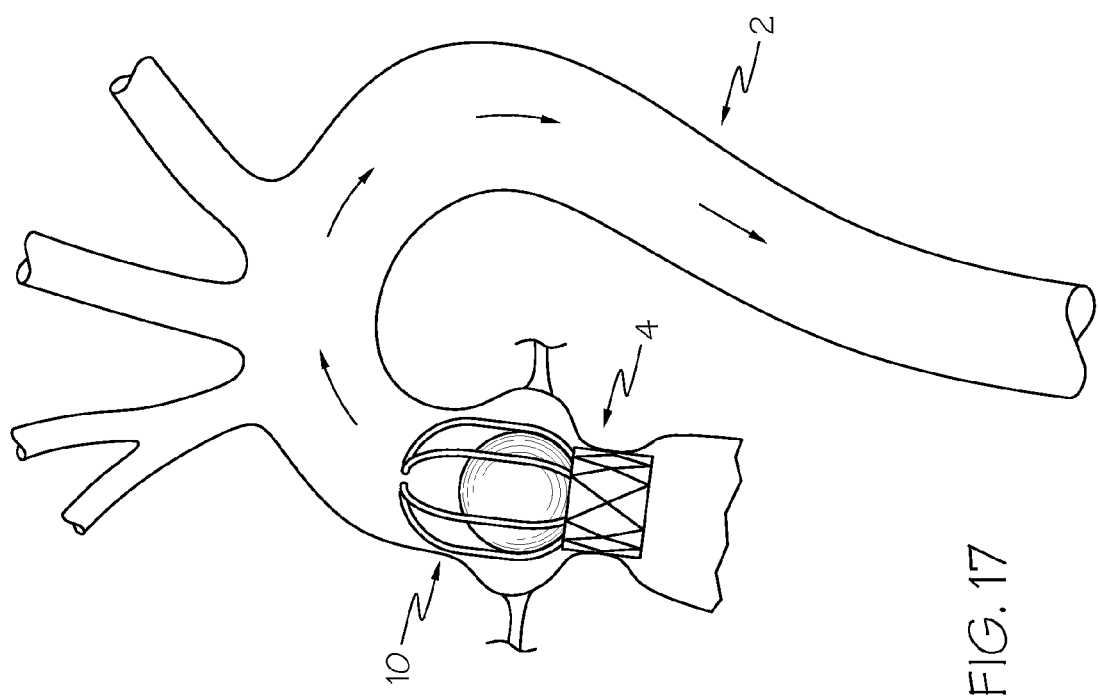
FIG. 17 is a view of the valve of FIG. 1 implanted at the site of a native valve.

In at least one embodiment, the valve 10 is implanted at the site of a native valve 4. In some embodiments, the native valve 4 is a heart valve. As shown in FIG. 17, the proximal end region 14 of the valve 10 is positioned at the native valve 4 of the heart to regulate flow into the aorta 2. Thus, in at least one embodiment, a portion of the valve body 22 is sized to fit securely at the base or annulus of the native valve. As used herein, the "annulus region" of the valve 10 is the portion of the valve positioned at the native valve annulus. The annulus region can also be considered an anchor region since the annulus region is the portion of the valve 10 that engages or anchors the valve to the body lumen. In some embodiments, the proximal end region 14 of the valve 10 is the annulus/anchor region. For example, when the valves 10 shown in FIGS. 1 and 3-8 are implanted, at least a portion of the proximal end region 14 of the valve 10 is positioned at the native valve annulus and therefore is the annulus/anchor region for the valve 10. In other embodiments, the middle region 16 of the valve body 22 is the annulus/anchor region. For example, when the valve 10 shown in FIG. 2 is implanted at least a portion of the middle region 16 of the valve body 22 is positioned at the native valve annulus. Thus, the middle region 16 of the valve 10 in FIG. 2 is the annulus/anchor region for the valve 10.

In use the valve 10 has a closed configuration and an open configuration. As used herein, the valve 10 is in the "closed configuration" when the lumen is occluded by the obstructer 40 and blood does not flow through the valve. Thus, the obstructer 40 can be described as being in a closed position when the valve 10 is in the closed configuration. An example of the valve 10 in the closed configuration is shown in FIG. 1. In at least one embodiment, when the valve is in the closed configuration a portion of the obstructer extends beyond the opening into the proximal region of reduced diameter. Thus a portion of the obstructer 40 is positioned within the lumen of the proximal end region 14 of the valve 10. This can be seen for example in FIG. 1 which shows the valve 10 in a closed configuration.

As used herein, the valve 10 is in the "open configuration" when the lumen 24 is not occluded by the obstructer 40 and blood flows through the lumen 24, around the obstructer 40, and out of the valve 10. Thus, the obstructer 40 can be described as being in an open position when the valve 10 is in the open configuration. An example of the valve 10 in the open configuration is shown in FIG. 6. The obstructer 40 is longitudinally moveable back and forth in a longitudinal direction within the lumen of the valve 10, as indicated by the bi-directional arrow in FIGS. 1-8. In at least one embodiment, the longitudinal movement of the obstructer 40 within the lumen 24 of the valve 10 is in response to the pressure of blood flow. In some embodiments, when the valve 10 is in an open configuration, the entire obstructer 40 is positioned outside of the proximal end region 14 of the valve 10. For example, as shown in FIGS. 6-7, the entire obstructer 40 is within the lumen of the middle region 16 of the valve 10 when the valve 10 is in the open configuration. For the valve embodiments shown for example in FIGS. 1 and 8, the entire obstructer 40 is within the distal end region 18 of the valve 10 when the valve 10 is in the open configuration.

In some embodiments, the region of the valve body 22 distal to the annulus/anchor region of the valve 10 has a maximum outer diameter that is less than the diameter of the lumen within which the valve 10 is implanted (not shown in FIG. 17). In one embodiment, this allows blood to exit from the lumen of the valve through the side openings 28 when the valve is in the open configuration.

In some embodiments, the valve 10 is "non directional" since each end of the valve 10 is configured to be a proximal end when the valve is implanted. FIGS. 6-7 show examples of a non directional valve 10. In other embodiments, the valve 10 is "unidirectional," where only one end of the valve 10 is configured to be a proximal end when the valve is implanted. FIGS. 1-5 and 8 show example of a unidirectional valve 10. Thus, the terms "unidirectional valve" and "non directional valve" as used herein do not refer to the flow of blood through the valve. This difference between a bidirectional valve and a non directional valve is relevant to the orientation of the valve in a delivery system.

Figure 5:
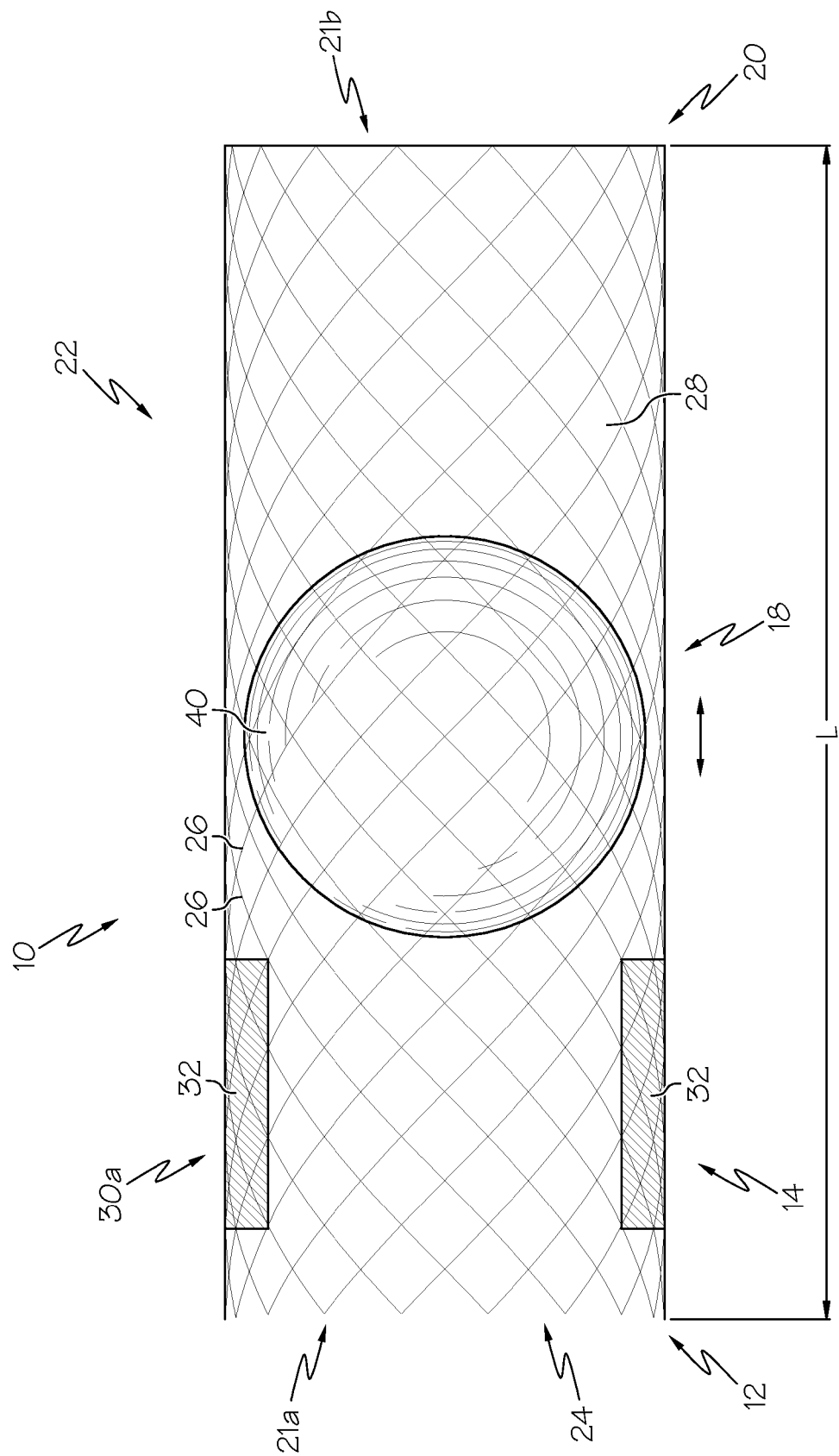
Figure 6:
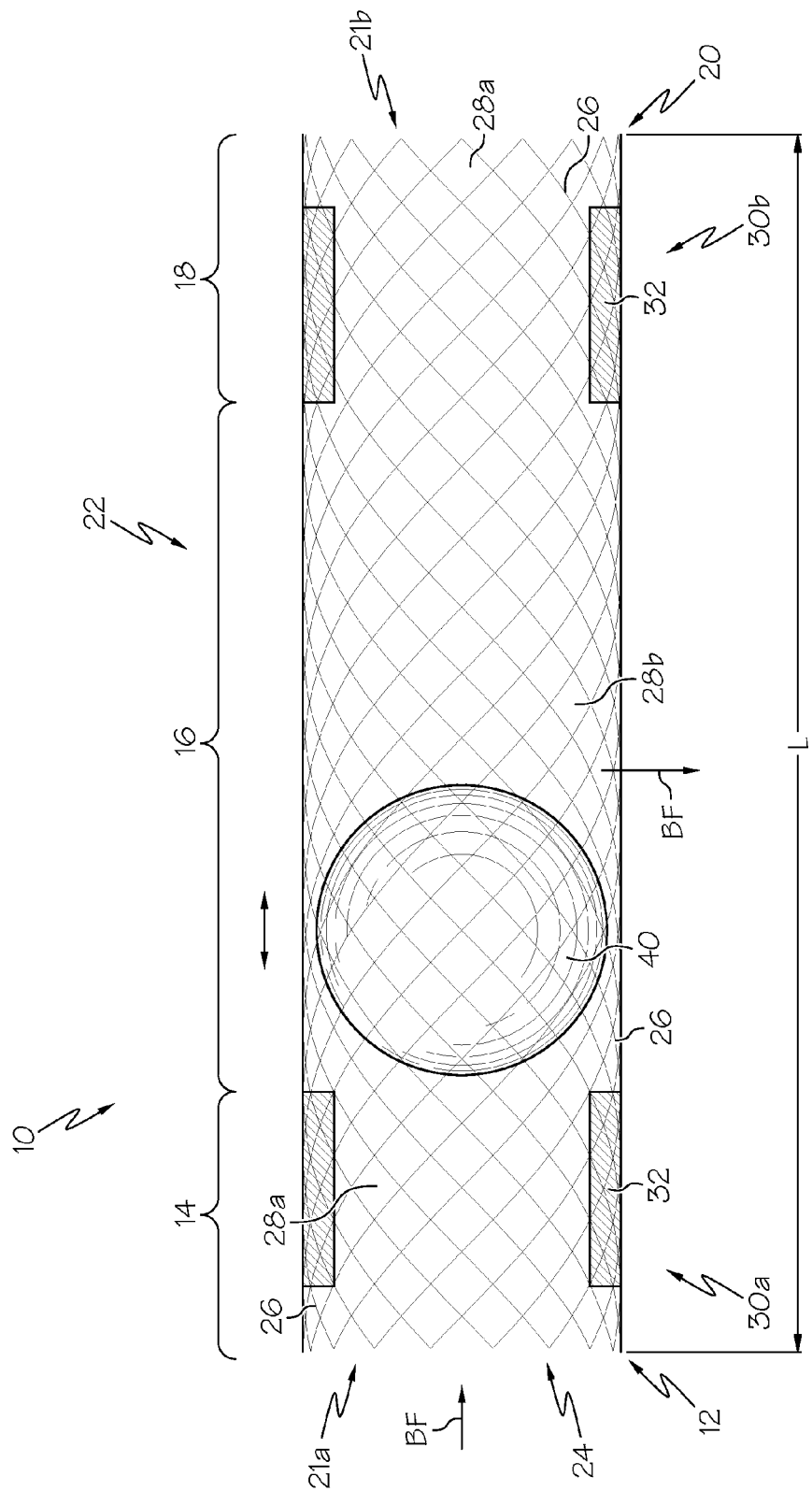
Figure 7:
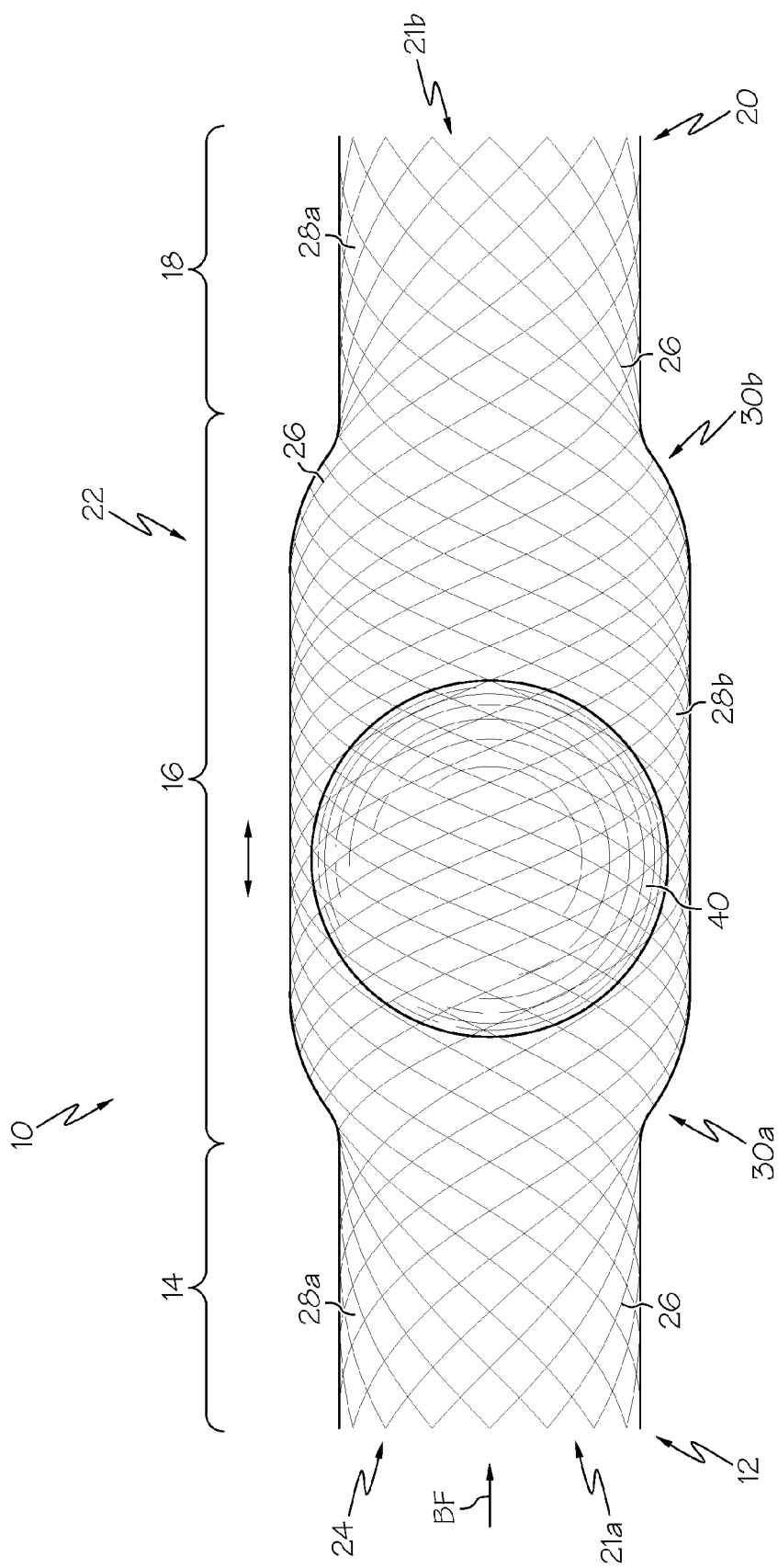

In some embodiments, the length (L) of the valve body 22 has substantially the same outer diameter, as shown for example in FIGS. 5-6. In other embodiments, a substantial portion of the length of the valve body 22 has substantially the same outer diameter and the ends of the valve body 22 are tapered, as shown for example in FIG. 2.

In at least one embodiment, the length of the valve body 22 has a first maximum outer diameter and a second maximum outer diameter different than the first maximum outer diameter. For example, as shown in FIG. 1, the proximal end region 14 of the valve body 22 has a first maximum outer diameter (D1) and the distal end region 18 of the valve body 22 has a second maximum outer diameter (D2) that is greater than the first maximum outer diameter. In one embodiment, the proximal end region 14 of the valve body 22 has a first maximum outer diameter, the middle region 16 of the valve body 22 has a second maximum outer diameter, and the distal end region 18 of the valve body 22 has a third maximum outer diameter where the second maximum outer diameter is greater than the first maximum outer diameter and the third maximum outer diameter. This is shown for example in FIG. 7.

In at least one embodiment, the valve 10 has at least one neck region 30. As used in this application, a "neck region" is a longitudinal region of reduced diameter compared to a longitudinally adjacent region of the valve body 22. In some embodiments, the valve 10 has only one neck region. This is shown for example in FIGS. 3 and 5. In other embodiments, the valve 10 has two neck regions 30, a proximal neck region 30a and a distal neck region 30b, longitudinally separated from one another, as shown for example, in FIGS. 1-2, 4, and 6-8.

In some embodiments, the neck region 30 is adjacent to a region that has a reduced diameter as compared to the adjacent region. This is shown for example by the neck region 30a in FIG. 3 that is positioned between the proximal end region 14 and the distal end region 18 and the proximal end region 14 has a reduced diameter as compared to the distal end region 18. In other embodiment, the neck region is a region of the valve 10. For example, the proximal end region 14 of the valve 10 in FIG. 1 can be described as a neck region because the diameter of the proximal end region 14 is less than the diameter of the distal end region 18 and less than the diameter of the obstructer 40.

In some embodiments, the neck region 30 is an area of reduced valve body 22 outer diameter and inner diameter, as shown for example in FIGS. 1 and 7 where both neck regions 30a, 30b are regions of reduced outer valve body diameter and reduced inner valve body diameter. In other embodiments, the neck region 30 is a region of reduced inner diameter, as shown for example, in FIGS. 5 and 6 where the neck regions 30a, 30b are regions of reduced inner valve body diameter while the outer valve body diameter is the same along the valve body length (L). In still further embodiments, the valve has a first neck region that is an area of reduced outer valve body diameter and a second neck region that is an area of reduced inner valve body diameter (not shown).

In at least one embodiment, the neck region(s) 30 maintain the obstructer 40 within the lumen 24 of the valve body 22 because the diameter of the obstructer 40 is greater than the diameter of the neck region(s) 30. In at least one embodiment, the proximal neck region 30a defines an opening that is occluded by the obstructer 40 when the valve 10 is in the closed configuration. This is shown for example in FIG. 1 where the opening at the distal end of the proximal end region 14 of the valve body 22 is occluded by the obstructer 40 when the valve 10 is in the closed configuration. As can be seen in FIGS. 1-8, the diameters of the valve body 22 at the neck regions 30 are each less than the diameter of the obstructer 40. For each valve 10 shown in FIGS. 1-2, 4, and 6-8, one neck region 30a can be described as forming a part of the proximal end region 14 and the other neck region 30b can be described as forming a part of the distal end region 18 of the valve body 22. Alternatively the neck regions 30a, and 30b of FIGS. 1-2, 4, and 6-8 can be described as being separate from and positioned between two regions 14, 16, 18 of the valve body 22.

In at least one embodiment, the reduced diameter of the neck region(s) 30 limits the longitudinal movement of the obstructer 40 within the lumen of the valve body 22 because the obstructer 40 has a diameter greater than the diameter of the neck region(s) 30. As shown in FIGS. 1-2, 4, and 6-8 a longitudinal distance separates the proximal neck region 30a and the distal neck region 30b. The longitudinal distance is sufficient for the obstructer 40 to move longitudinally between an open valve position and a closed valve position. In at least one embodiment, the longitudinal distance is greater than the diameter (Do) of the obstructer 40. In some embodiments, the longitudinal distance is between 1.5 times the obstructer diameter to 2 times the obstructer diameter.

Figure 4:
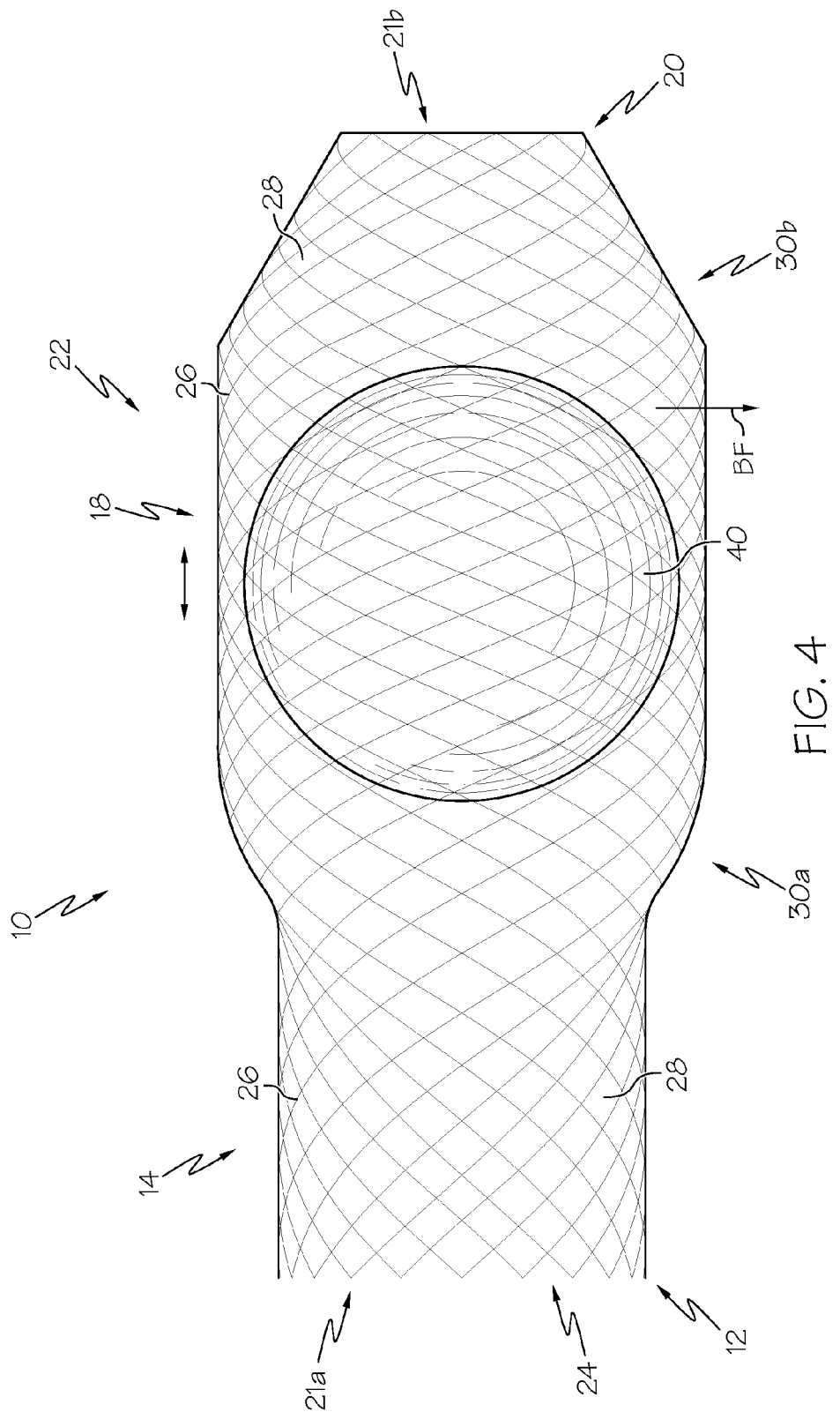

In at least one embodiment, the neck region 30 has a variable diameter and is sloped or curved. For example, the proximal neck region 30a in FIG. 4 is curved and the distal neck region 30b in FIG. 4 is sloped. As used herein "curved" indicates a variable angle relative to the longitudinal axis of the valve 10 and "sloped" indicates a constant angle relative to the longitudinal axis of the valve 10. In some embodiments, the proximal and distal neck regions 30a, 30b are both curved or both sloped. For example the proximal and distal neck regions 30a, 30b in FIG. 7 are curved. The two curved or sloped neck regions 30a, 30b can have the same variable angle or different variable angles relative to the longitudinal axis of the valve 10. In other embodiments, one of the proximal neck region 30a and the distal neck region 30b is curved and the other is sloped, as shown for example in FIG. 4 where the proximal neck region 30a is curved and the distal neck region 30b is sloped.

In at least one embodiment, the neck region 30 comprises at least one stop 32. In some embodiments, the stop(s) is affixed to the inner surface of the valve body 22. As used herein "affixed" is a permanent attachment. Suitable methods for affixing include but not limited to, soldering, welding, adhesive, and any combinations thereof.

FIGS. 5-6 show a valve with neck region(s) 30 comprising at least one stop 32. Each stop 32 includes an outer surface, an inner surface, a longitudinal extent, a circumferential extent, and a thickness. The thickness is measured from the outer surface to the inner surface of the stop. Although the stops 32 shown in the figures have a constant thickness, the stops can have a variable thickness. For example, the stops can be tapered or curved with one end of the stop having a greater thickness than the other end of the stop. In some embodiments, the circumferential extent of a stop 32 is at most equal to the circumferential extent of the inner surface of the valve body 22. In at least one embodiment, the stop 32 extending around the entire inner circumference of the valve body 22 is an expandable ring. Each neck region 30 can have one, two, three, four, five, six, seven, eight, or more stops 32, each extending around at least a portion of the inner circumference of the valve body 22. The neck regions 30 of a valve 10 with two or more neck regions can have the same or different number of stops 32, the same or different stop configurations, and combinations thereof.

In some embodiments, a neck region 30 comprising at least one stop has a constant diameter. For example, a neck region 30 with one stop having a constant thickness and a circumferential extent equal to the circumferential extent of the inner surface of the valve body has a constant diameter. In other embodiments, a neck region 30 comprising at least one stop 32 has a variable diameter. One example of a neck region with a variable diameter is a neck region 30 with one stop 32 that extends about only a portion of the circumferential extent of the inner surface of the valve body. Another example of a neck region with a variable diameter is a neck region 30 with a plurality of spaced apart stops positioned about the inner surface of the valve body. Yet another example of a neck region with a variable diameter is where the stop 32 is tapered or curved.

As shown in FIGS. 5-6, the stops 32 are positioned a distance away form the proximal and distal ends 12, 20 of the valve body 22. In some embodiments, the stops extend to the ends 12, 20 of the valve body 22 such that the proximal end of a proximal stop is positioned at the proximal end of the valve body 22 and the distal end of a distal stop is positioned at the distal end of the valve body 22 (not shown). In one embodiment, the proximal stop(s) extend the length of the proximal end region and distal stop(s) extend the length of the distal end region of the valve body 22 (not shown).

In at least one embodiment, a substantial portion of the length of the valve body 22 has the same outer diameter between the proximal and distal neck regions 30a, 30b and the same inner diameter between the proximal and distal neck regions 30a, 30b. This is shown for example in FIG. 2 where the outer and inner diameters of the middle region 16 are the same as the outer and inner diameters of a portion of the distal end region 18.

In some embodiments, inner diameter of the anchor region of the valve 10 is larger than the diameter of the obstructer 40, as shown for example in FIG. 2 where the middle region 16 is the anchor region. In these embodiments, the obstructer 40 moves longitudinally between the two neck regions 30a, 30b positioned on either side of the anchor region and within the lumen of the anchor region. In this valve embodiment, the obstructer 40 does not repeatedly hit the anchor region, middle region 16, as the valve 10 moves between the open and closed configuration, as compared to the valve embodiment shown in FIG. 1 where the obstructer 40 repeatedly hits the anchor region, proximal end region 14. In some embodiments, a valve 10 with an obstructer 40 that does not repeatedly hit the anchor region as the valve 10 moves between the open and closed configuration improves the durability of anchor region.

As shown in FIG. 2, the elements 26 forming the proximal end region 14 curve from the middle region 16 towards the end ring 25 defining the end lumen opening 21a of the proximal end 12. In at least one embodiment, the proximal end 12 of the valve 10 shown in FIG. 2 has the configuration of the distal end 20 shown in FIG. 9. In some embodiments, a distal portion of the proximal end region 14 has an outer diameter the same as the middle region 16 (not shown). In this embodiment, the elements 26 forming the proximal end region 14 do not curve from the middle region 16 to the proximal end 12 but instead include a straight portion that extends from the middle region 16 to a curved portion of the element 26 where the curved portion extends to the end of the valve 10.

In at least one embodiment, the length of the valve body 22 includes a first maximum inner diameter and second maximum diameter different than the first maximum inner diameter. In at least one embodiment, the first maximum inner diameter defines an opening that is occluded by the obstructer 40 when the valve 10 is in the closed configuration. For example the valve 10 in FIG. 1 has a proximal end region 14 of the valve body 22 with a first maximum inner diameter and a distal end region 18 of the valve body 22 with a second maximum inner diameter that is greater than the first maximum inner diameter. In some embodiments, the first maximum inner diameter defining an opening that is occluded by the obstructer 40 is a proximal neck region 30a, as shown for example in FIG. 1. As an additional example, the valve 10 in FIG. 7 has a proximal end region 14 with a first maximum inner diameter, a middle region 16 with a second maximum inner diameter, and a distal end region 18 with a third maximum inner diameter, where the second maximum inner diameter is greater than the first maximum inner diameter and the third maximum inner diameter.

In some embodiments, the valve (not shown) has a proximal end region 14 and a middle region 16 as shown in FIG. 7 and a distal end region 18 as shown in FIG. 6. In other embodiments, the valve (not shown) has a proximal end region 14 and a middle region 16 as shown in FIG. 6 and a distal end region 18 as shown in FIG. 7.

The proximal and distal ends 12, 20 of the valve body 22 each define an end lumen opening 21. The proximal end lumen opening 21a of the valve body 22 is sized to allow blood to enter the lumen of the valve 10. The distal end lumen opening 21b is sized for a collapsed obstructer 40 to pass through the end lumen opening 21 and into the lumen of the valve body 22 during deployment of the valve 10 and also sized to maintain the expanded obstructer 40 in the lumen of the valve body. In at least one embodiment, the diameters of the end lumen openings 21a and 21b are each smaller than the diameter of the obstructer 40. In some embodiments, the end lumen opening 21a defined by the proximal end 12 of the valve body 22 is larger than the end lumen opening 21b defined by the distal end 20 of the valve body 22. In one embodiment, the diameter of the proximal end lumen opening 21a is greater than the diameter of the distal end lumen opening 21b. In other embodiments, the end lumen openings 21a and 21b are the same size. In one embodiment, the diameters of the end lumen openings 21a and 21b are the same.

Figure 11:
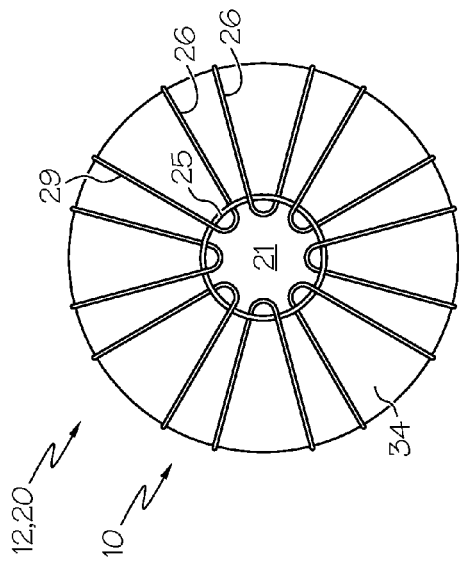
FIGS. 9-11 show end views of a valve.
Figure 10:
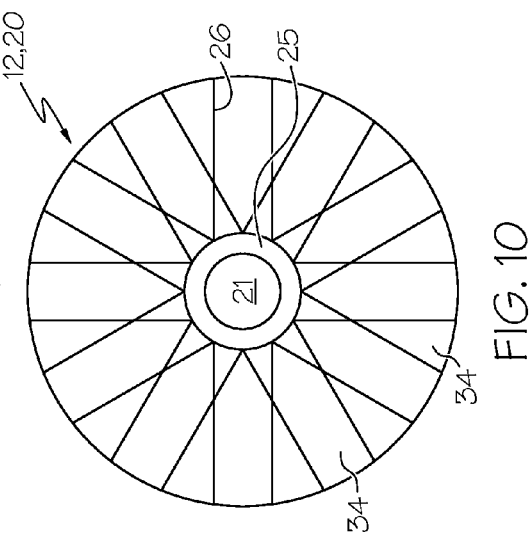
Figure 9:
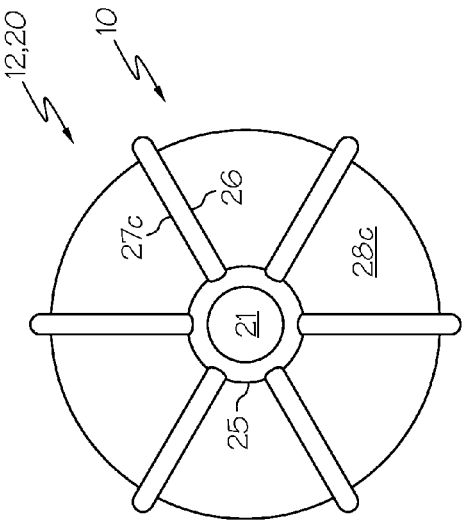

In at least one embodiment, one or both of the ends 12, 20 of the valve 10 include a plurality of elements 26 and an end ring 25. FIGS. 9-11 are exemplary views of an end 12, 20 of a valve 10 that includes a plurality of elements 26 and an end ring 25. In some embodiments, the elements 26 forming an end region 14, 18 of the valve 10 are either affixed to an end ring 25, as shown for example in FIGS. 9-10. In other embodiments, the ends of the elements are affixed to one another to form an end ring 25 (not shown). In at least one embodiment, the end ring 25 includes a first ring and a second ring where the ends of the elements are between, and affixed to, the first and second rings.

As can be seen in the figures, the end ring 25 defines the end lumen opening 21. In some embodiments, the diameter of the end ring 25 is less than the diameter of the valve body 22 at that end. In at least one embodiment, the end ring 25 is non-expandable. FIG. 9 is an example of a suitable configuration for the distal end 20 of the valve shown in FIG. 1 and for the proximal and distal ends of the valve 10 shown in FIG. 2. FIG. 10 is an example of a suitable configuration of the distal ends 20 of the valves 10 shown in FIGS. 3 and 5. FIG. 11 is an example of a suitable configuration of the distal end 20 of the valve 10 shown in FIG. 8. As can be seen in FIGS. 9-11, the ends also include a plurality of end openings 34. In at least one embodiment, the end openings 34 are sized to allow blood to flow therethrough.

In at least one embodiment, the valve body 22 defines a plurality of side openings 28. In some embodiments, the side openings 28 located in one section of the valve body 22 have a larger size than the side openings 28 located in at least one other section of the valve body 22. In some embodiments, the distal end region 18 includes smaller side openings 28, as shown for example in FIG. 4. In other embodiments, the proximal end region 14 includes smaller side openings 28.

In at least one embodiment, blood flows from the lumen 24 of the implanted valve 10 through the larger sized side openings 28 into the body lumen. In some embodiments, the larger sized side openings 28 are located between the anchor region of the valve and the open position of the obstructer 40. In at least one embodiment, the region(s) defining the larger sized side openings 28 have fewer elements than the region(s) defining the smaller sized side openings 28. For example, the valve 10 in FIG. 1 has first side openings 28a that have a first size and second side openings 28b that have a second size where the second size is larger than the first size. The arrows (BF) indicate the flow of blood out of the lumen of the valve 10 through the second side openings 28b. Also as shown in FIG. 1, the distal end region 18 of the valve has fewer elements 26 than the proximal end region 14.

In at least one embodiment, the larger sized side openings 28 are defined by a plurality of elements 26 that are spaced apart from one another and distributed about the circumference of the valve body 22. Although the spaced apart elements 26 are shown as being substantially parallel to the longitudinal axis of the valve 10, it is within the scope for the spaced apart elements 26 to extend helically around the longitudinal axis of the valve 10. Additionally, although the spaced apart elements 26 in FIG. 1 are shown as being substantially parallel to one another, in some embodiments the spaced apart elements are not parallel to one another (not shown).

In at least one embodiment, one or more of the elements 26b defining the larger sized side openings 28b has a first end region 27a a first distance from the longitudinal axis of the valve 10, a middle region 27b a second distance from the longitudinal axis of the valve, and a second end region 27c a third distance from the longitudinal axis of the valve. This is shown for example in FIG. 1. In some embodiments, the first and third distances are variable distances from the longitudinal axis of the valve 10 and the second distance is a constant distance from the longitudinal axis of the valve 10. As can be seen in FIG. 1, the end regions 27a,c of the elements 26b in the distal end region 18 of the valve 10 are at an angle relative to the longitudinal axis of the valve 10. In some embodiments, the end regions 27a,c have a configuration that is complementary to the shape of the obstructer 40. In at least one embodiment, the inner diameter of the lumen defined by the middle regions 27b of the elements 26b is greater than the diameter of the obstructer 40 so that the obstructer 40 can move longitudinally along the length of the middle regions 27b of the elements 26b. In some embodiments, the length of the first end region 27a is less than the length of the second end region 27c.

In some embodiments, the neck region, located within the proximal end region of the valve body, has a first inner diameter; the obstructer has a second diameter larger than the first inner diameter of the neck region, the obstructer longitudinally moveable within a first portion of the lumen of the valve body; and the first portion of the lumen has an inner lumen diameter greater than the second diameter. In one embodiment, when the valve is in the open configuration, blood flows through the neck region, around the obstructer within the first portion of the lumen, and exits the valve at the distal end, since the diameter of the first portion of the lumen of the valve body is greater than the diameter of the obstructer. For this embodiment, the valve can have the same sized openings along the length of the valve body and the openings do not need to be configured to permit blood to flow out of the valve lumen through the openings.

In at least one embodiment, the obstructer 40 is positioned between the proximal end 12 and the distal end 20 of the valve 10. This is shown for example in FIGS. 1-8. As shown in FIGS. 1-8, the obstructer 40 is entirely within the lumen of the valve 10 so that no portion of the obstructer 40 extends beyond the ends 12, 20 of the valve 10. In some embodiments, the obstructer 40 has an outer diameter that is greater than the maximum inner diameter of the proximal end region 14, the distal end region 18, or both the proximal end region 14 and the distal end region 18. The obstructer 40 shown in FIGS. 1 and 7 has an outer diameter that is greater than the maximum inner diameter of the proximal end region 14 of the valve body 22. In some embodiments, as shown in FIG. 6, the outer diameter of the obstructer 40 is also greater than the maximum inner diameter of the distal end region 18 of the valve body 22. In FIG. 5, the obstructer 40 has an outer diameter that is greater than the inner diameter of the valve body 22 at the stops 32.

In at least one embodiment, the obstructer 40 is expandable and collapsible. In some embodiments, the obstructer 40 is a ball. In other embodiments, the obstructer 40 is an expandable balloon. In at least one embodiment, the obstructer 40 has a port 42 through which expansion media is introduced into the lumen of the obstructer 40. This is shown for example in FIG. 16. In some embodiments, the expansion media expands the obstructer 40. Although the expansion media can be any suitable material, in at least one embodiment, the expansion media is a silicone liquid. In some embodiments, the port 42 is an injection port for a needle 68 and provides an entry point for the needle 68 to enter the lumen of the obstructer 40 to inject the expansion media into the obstructer 40. In one embodiment the needle is pre-loaded into the injection port for delivery and the needle is removed from the injection port after the obstructer is expanded. This is shown for example in FIG. 14.

In at least one embodiment, the valve body 22 has a cover 50 affixed thereto. The cover 50 can also be considered to be a liner or a skirt. In some embodiments, the cover 50 is located at only at the anchor or annulus region. This is shown for example in FIG. 1 where the cover is affixed only to the proximal end region 14 which is the anchor region of this valve embodiment and in FIG. 2 where the cover 50 is affixed only to the middle region 16 of the valve body 22. In at least one embodiment, the cover 50 prevents blood from leaking through the side openings 28 of the proximal end region 14 of the valve body 22. In some embodiments, the cover 50 is comprises an impermeable material. The cover 50 can be affixed to the outer surface of the valve body 22, the inner surface of the valve body 22 as shown in FIGS. 1-2, or both the outer surface and the inner surface of the valve body 22.

In at least one embodiment, the valve body 22 has an impermeable section and a permeable section longitudinally adjacent to the impermeable section. This is shown for example in FIG. 1 where the proximal end region 14 is an impermeable section and the distal end region 18 is a permeable section. Thus, blood cannot flow from the lumen 24 through side openings 28 of the proximal end region 14 but can flow from the lumen 24 through the side openings 28 of the distal end region 18. In some embodiments, the side openings 28 in the impermeable section are sized to prevent blood flowing therethrough while the side openings 28 in the permeable section are sized to allow blood to flow therethrough. In at least one embodiment, the cover 50 is made of a material that is impermeable. Thus, in some embodiments, the impermeable section of the valve body has an impermeable cover 50 affixed thereto.

Figure 8:
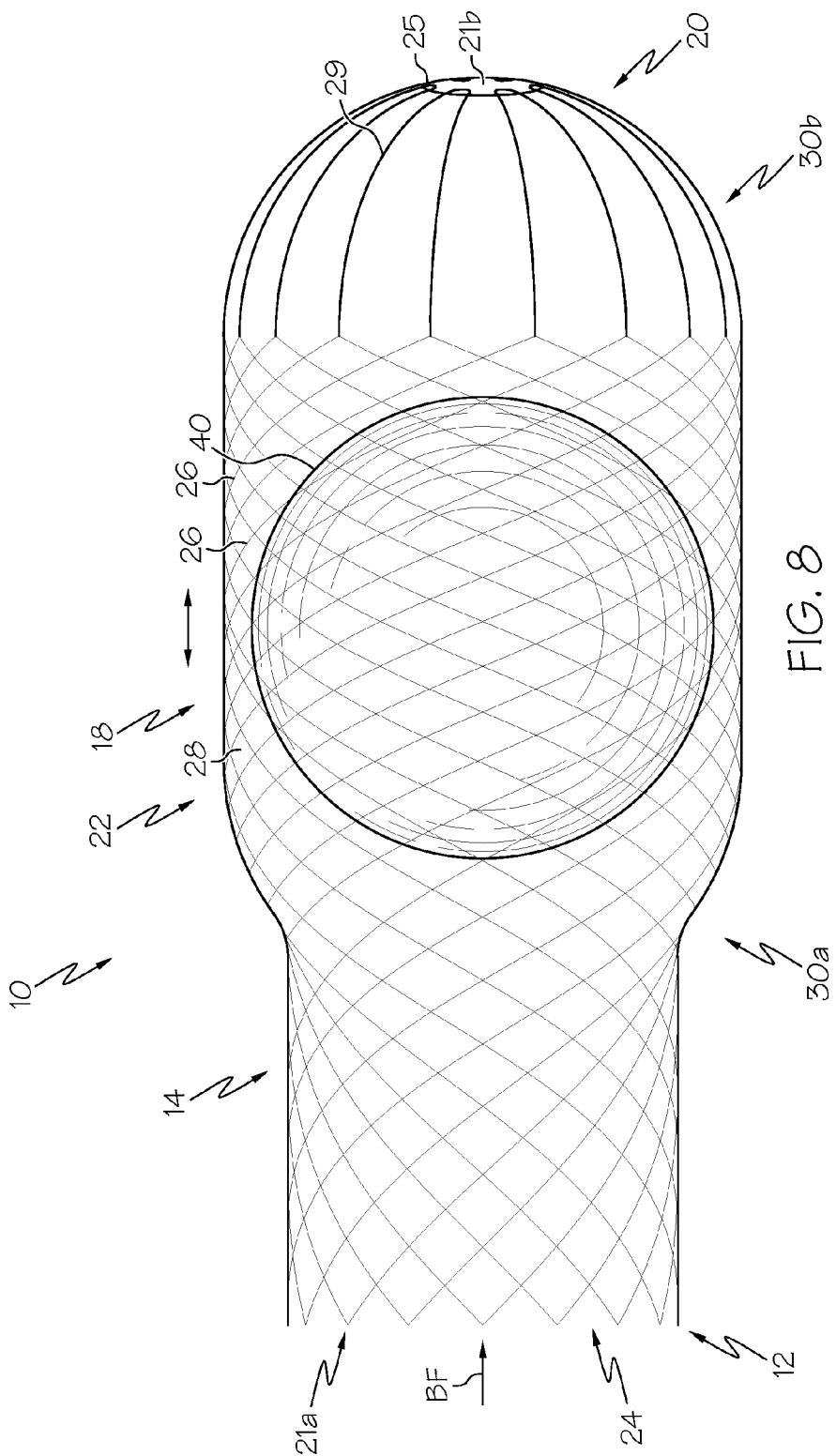

In at least one embodiment, at least a portion of the valve body 22 is an expandable mesh formed by braiding, weaving, and/or knitting one or more elements 26. For example, the valve body 22 shown in FIG. 8 is an expandable mesh that extends from the proximal end 12 to the distal end 20. In some embodiments, the expandable mesh has a plurality of end loops 29 at one or both of the ends 12, 20. Details for forming end loops 29 can be found in U.S. Pat. No. 7,462,192 to Norton et al; U.S. Pat. No. 7,655,039 to Leanna et al; and U.S. Pat. No. 8,151,682 to Liburn et al, the contents of each are incorporated by reference. In at least one embodiment, the end loops 29 are elongated. One example of elongated end loops 29 is shown in FIG. 8. In some embodiments, the elongate end loops 29 define openings sized to allow blood to flow therethrough.

In at least one embodiment, the element(s) 26 are braided on a mandrel that has a variable diameter to form a valve body 22 with a variable diameter, such as the valve body 22 shown in FIG. 7. In some embodiments, the element(s) 26 are braided on a mandrel that has a variable diameter to form the neck region(s) 30 of the valve 10. In at least one embodiment, the neck region(s) 30 for the valve 10 are formed in a tubular expandable mesh by a shaped mandrel.

In other embodiments, at least a portion of the valve body 22 is an expandable network of interconnected elements 26 formed by cutting or etching the elements 26 from a tubular stock, or by cutting or etching the elements 26 from a flat sheet which is subsequently rolled into a tube. For example, in at least one embodiment, the elements 26 forming each of the valves 10 shown in FIGS. 1-7 are cut or etched from a tube of material. In at least one embodiment, the neck region(s) 30 for the valve 10 are formed in an expandable network of interconnected elements 26 by a shaped mandrel.

An expandable mesh portion of a valve described herein could be formed as an expandable network of interconnected elements and vice versa. Thus, for example, the valve bodies 22, or portions thereof, shown in the figures can be formed by braiding, weaving, and/or knitting one or more elements 26, or by cutting or etching the elements from a tube or flat sheet of material.

As discussed above, in at least one embodiment one or both ends 12, 20 of the valve 10 includes an end ring 25. One example of a valve end 12, 20 with an end 25 ring is shown in FIG. 11. In at least one embodiment, the end ring 25 shown in FIG. 11 interconnects the end loops 29 of expandable mesh forming the valve body 22 by extending through the end loops 29. In one embodiment, the two ends of the end ring 25 are affixed to one another after the end ring 25 is extended through the end loops 29. In some embodiments, one or more of the end loops 29 are moveable relative to the end ring 25. In one embodiment, the end loops 29 move relative to the end ring 25 when the valve body 22 is expanded. In other embodiments, the each end loop 29 is affixed to the end ring 25. In at least one embodiment, the end ring 25 does not extend through the end loops 29 but is otherwise affixed to the end loops 29 (not shown). For example, in some embodiments, the end ring 25 is affixed to the one of the inner or outer surfaces of the end loops 29.

Figure 12:
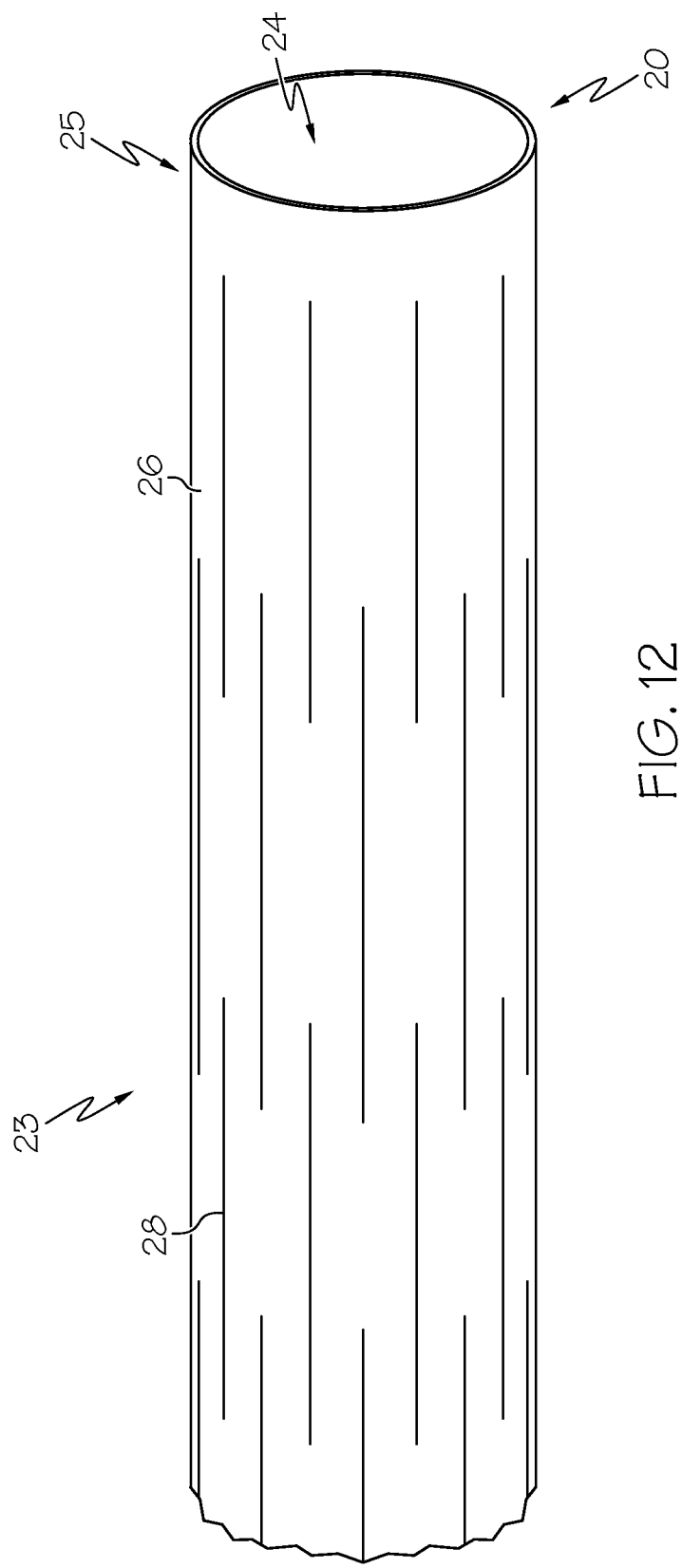
FIG. 12 is view of a tube in an as cut state.
Figure 13:
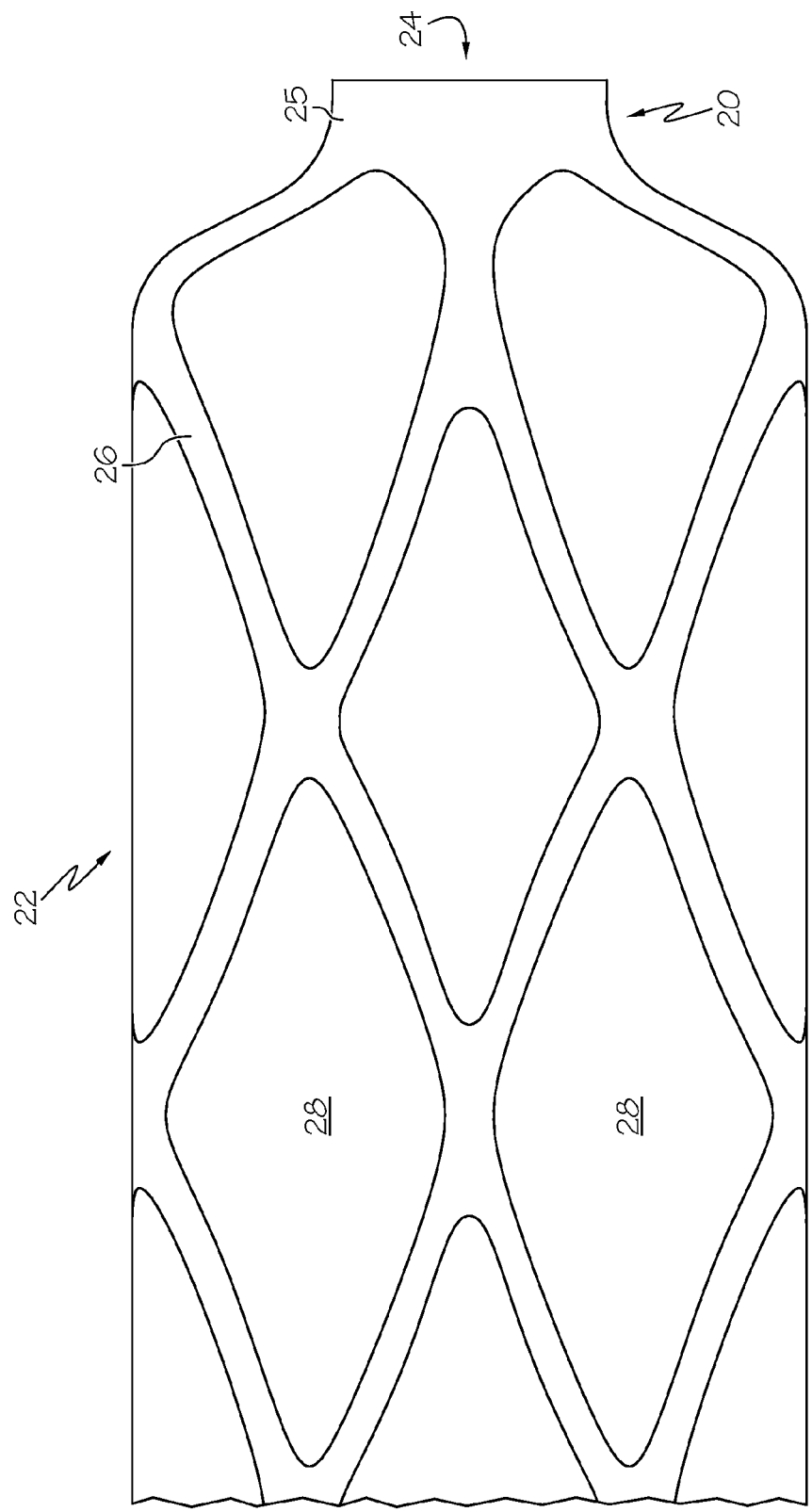
FIG. 13 is view of the tube in FIG. 12 in expanded state.

In at least one embodiment, one or more end rings 25 in addition to the elements 26 are cut or etched into a tube or flat sheet of valve material. In some embodiments, the elements 26 and the end rings 25 have different expansion characteristics. In one embodiment, the elements 26 are expandable and the end ring 25 is non-expandable. This is shown for example in FIGS. 12-13. FIG. 12 shows a portion of a tube 23 with elements 26 and an end ring 25 that have been cut or etched in the tube. Thus, the tube 23 is in a as cut state. FIG. 13 shows the tube 23 of FIG. 12 in an expanded state. As can be seen in FIGS. 12-13, the diameter of the end ring 25 is the same in the as cut state and in the expanded state. In some embodiments, the tube 23 is cut or etched to form only a portion of the valve body 22. In other embodiments, the tube 23 is cut or etched to form the entire valve body 22. In at least one embodiment, a plurality of tubes are each cut or etched to form a portion of the valve body; the tubes are affixed to one another; and expanded to form the valve body. In some embodiments, the tubes are affixed to one another to form a valve body and then the valve body is expanded. In other embodiments, the tubes are expanded and then affixed to one another to form a valve body.

In some embodiments a valve is made by 1) cutting or etching the elements 26 and one or more end rings 25 from a tube comprising a shape memory alloy, with one end ring 25 forming the distal end of the tube, such as shown in FIG. 1 and the other end ring 25 forming the proximal end of the tube, such as shown in FIG. 2; modifying the tube into a valve body with a desired final shape using a shaped mandrel; and processing the valve body to have superelastic properties so that the desired final shape is obtained at implantation.

Figure 3:
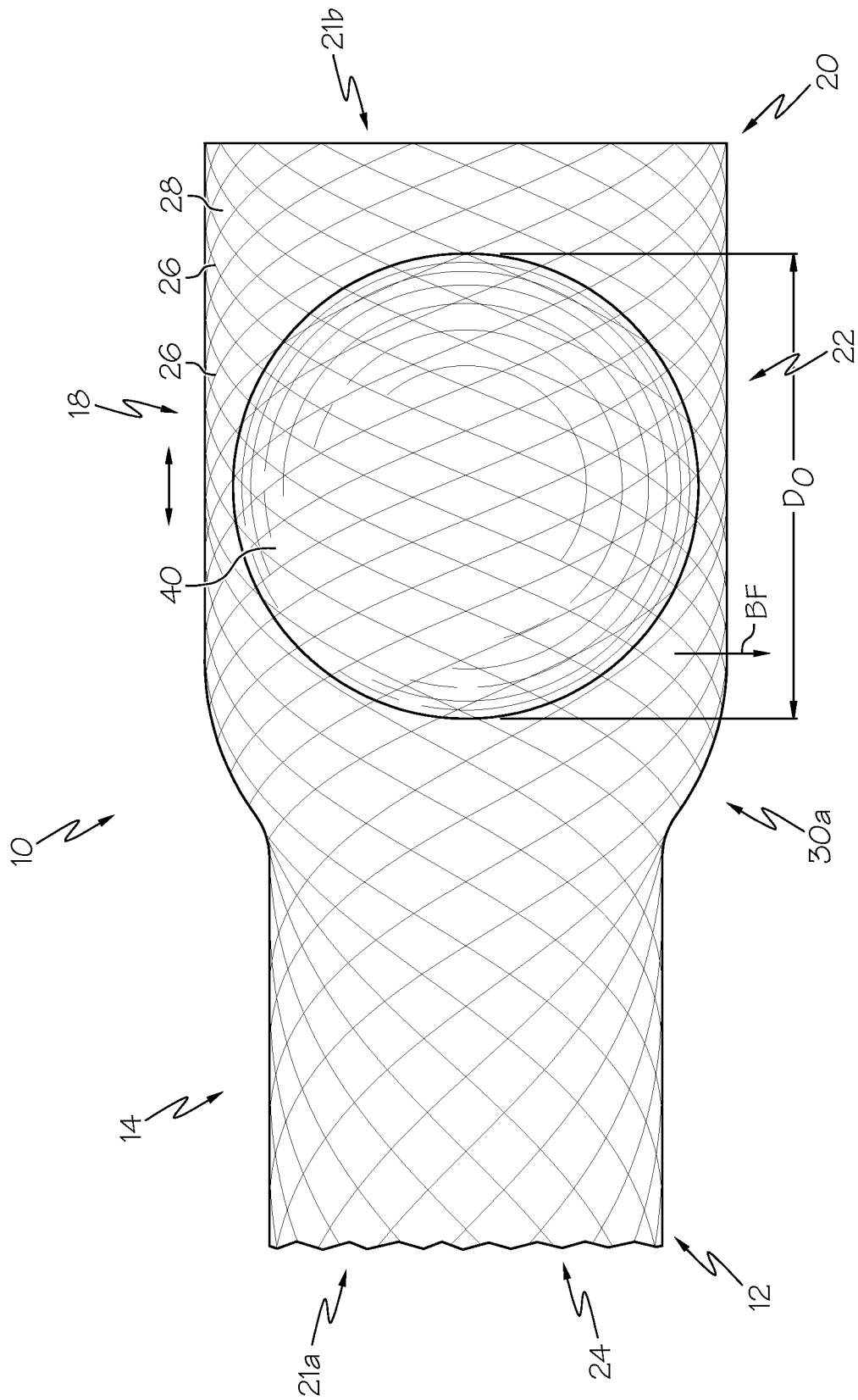

FIG. 10 shows an exemplary configuration for the end(s) 12, 20 of a valve 10, for example for the distal ends 20 of the valves shown in FIGS. 3 and 5. In some embodiments, to form the distal end 20 of the valve body 22 shown in FIGS. 3 and 5, the cut or etched elements 26 at the distal end region of tubular stock are bent inwards at an oblique angle to the longitudinal axis of the tubular stock and are either affixed to an end ring 25, or affixed to one another thereby forming an end ring 25. In some embodiments, the elements 26 are bent approximately 90° inwards relative to the longitudinal axis of the valve body 22 to form the distal end 20 of the valve body 22, as shown for example in FIGS. 3 and 5.

In at least one embodiment the end(s) 12, 20 are open. An end that is open defines a single opening in contrast to an end 12, 20 with an end ring 25. For example the proximal end 12 of the valves 10 in FIGS. 1 and 3-8 are open and the distal end of the valves 10 in FIGS. 4 and 6-7 are open. As can be seen from these figures, the ends 12, 20 do not have an end ring 25 or elements 26 extending towards the longitudinal axis of the valve 10.

In at least one embodiment, the expandable mesh and the expandable tubular network of interconnected elements 26 is a stent. For example, the proximal end region 14 of the valve body 22 of the valve 10 shown in FIG. 1 is a stent and the middle region 16 of the valve body 22 of the valve 10 shown in FIG. 2 is a stent. In some embodiments, the entire valve body 22 is a stent. This is shown for example in FIGS. 3-8.

The valve body 22, the elements 26, end ring(s) 25, and/or the stop(s) 32 may be made from any suitable non-biodegradabale biocompatible material(s) including one or more polymers, one or more metals or combinations of polymer(s) and metal(s). Polymers that may be used include polyester, polyamide, polyoxymethylene, polyurethane, silicone, polycarbonate, various copolymers such as but not limited to polyetherester, polyetheramide, and combinations thereof. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The valve body 22, the elements 26, end ring(s) 25, and/or the stop(s) 32 may be made of shape memory materials, such as Nitinol, or may be made of materials which are plastically deformable. In the case of shape memory alloys, the shape memory alloy forming the valve body 22 may be provided with shape memory effect properties or superelastic properties, as is known in the art. A valve body 22 made of a shape memory alloy with shape memory effect properties restores itself to its memorized shape upon being heated to a transition temperature and having any restraints removed therefrom. A valve body 22 made of a shape memory alloy with superelastic properties reverts to a prior configuration upon removal of a load.

Materials that can be used to make the cover 50 include but are not limited to, polyamide, silicone, polystyrene-polyisobutylene-polystyrene triblock copolymer (SIBS), polyurethane, polyethylene terephthalate (PET), expanded polytetrafluoroethylene (ePTFE), and any combination thereof. In at least one embodiment, the cover 50 is an elastic or conforming polymeric covering.

As discussed above, at least a portion of the valve body 22 may be created by methods including cutting or etching a design from a tubular stock, from a flat sheet which is cut or etched and which is subsequently rolled, or from one or more interwoven wires or braids. Any other suitable technique which is known in the art or which is subsequently developed may also be used to manufacture the valve body disclosed herein. The elements 26 of the valve body 22 can form any pattern or have any arrangement.

In some embodiments, the first portion valve body is made by a first method, the second portion is made by a second method, and the first and second portions are attached to one another to form the valve body. For example, the proximal end region 14 of the valve body 22 similar to that shown in FIG. 1 can be made by weaving, braiding, knitting the elements 26; the distal end region 18 made by forming each of the plurality of elements 26 and one end of each of the plurality of elements 26 is affixed to the proximal end region 14. In some embodiments, the other ends of each of the plurality of elements 26 of the distal end region are further affixed to one another to form the valve body 22, as shown in FIG. 1.

In at least one embodiment, the obstructer 40 is made of a biocompatible material. In at least one embodiment, the obstructer 40 is made of a polymeric material. In at least one embodiment, the obstructer 40 is manufactured from compliant material for example, but not limited to, nylon, silicones, and polyamines. In at least one embodiment, the obstructer 40 is made of semi-compliant material, for example, but not limited to, ethylene-vinyl acetate, olefin copolymers or homopolymers, polyethylenes, polyurethanes, crosslinked low density polyethylenes (PETs), highly irradiated linear low density polyethylene (LDPE), acrylonitrile polymers and copolymers, acrylonitrile blends and ionomer resins. In at least one embodiment, the obstructer 40 is manufactured from non-compliant material, for example, but not limited to, polyethylene terephthalates, polyacrylenesulfide, polyoxymethylene and polyoxymethylene copolymers, and polyesters and polyester copolymers. Other materials may also be used for the obstructer 40. In some embodiments, the obstructer 40 is made a plurality of layers of different materials. In at least one embodiment, the obstructer 40 has a coating on the exterior surface. In some embodiments, the coating includes a therapeutic agent. In other embodiments, the coating includes a lubricious agent.

In some embodiments the valve 10, the delivery system 60 or other portion of the assembly may include one or more areas, bands, coatings, members, etc. that is (are) detectable by imaging modalities such as X-Ray, MRI, ultrasound, etc. In some embodiments at least a portion of the valve 10 is at least partially radiopaque. For example, in at least one embodiment, the anchor region of the valves 10 disclosed herein includes at least one area, band, coating, or member that is detectable by imaging modalities.

In some embodiments the at least a portion of the valve 10 is configured to include one or more mechanisms for the delivery of a therapeutic agent. Often the agent will be in the form of a coating or other layer (or layers) of material placed on a surface region of the valve, which is adapted to be released at the site of the valve's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate. Suitable lubricious agents include, but are not limited to, silicones, polyvinyl pyrrolidone, PPO (polypropylene oxide), BioSlide™, hydrogels such as PEG (polyethylene glycol), PEO/PPO/PEO-polyethylene oxide/polypropylene oxide/polyethylene oxide triblock polymer manufactured by BASF or PPO/PEO/PPO, and combinations thereof. BioSlide™ is a hydrophilic, lubricious coating comprising polyethylene oxide and neopentyl glycol diacrylate polymerized in a solution of water and isopropyl alcohol in the presence of a photoinitiator such as azobisisobutronitrile.

B. Delivery System and Method of Delivering the Valve

In at least one embodiment, the valve 10 is collapsed, inserted or loaded into a delivery system 60, and delivered to a site of implantation. An example of a delivery system 60 is shown in FIGS. 14-15. In at least one embodiment, the delivery system 60 includes an outer sheath 62 defining a lumen 63; an intermediate shaft 64 defining a lumen 65; an inner shaft 66 defining a lumen 67; a needle 68 at the distal end of the inner shaft 66, the needle 68 defining a lumen; a handle 70; and a reservoir 72. In some embodiments, the intermediate shaft 64 is a push rod. For example, as discussed below, when the intermediate shaft 64 is used to push the valve 10 out of the lumen of the outer sheath 62, the intermediate shaft functions as a push rod. As shown in FIG. 14, the inner shaft 66 is positioned within the lumen 65 of the intermediate shaft 64 and the intermediate shaft 64 is positioned within the lumen 63 of the outer sheath 62.

In at least one embodiment, the outer sheath 62 has a handle 70 located at the proximal end of the outer sheath 62 as shown in FIG. 14. In some embodiments, the intermediate shaft 64 has a handle 70 located at the proximal end of the intermediate shaft 64. In some embodiments, the outer sheath 62 is longitudinally moveable relative to the intermediate shaft 64 and the inner shaft 66. In one embodiment, the outer sheath 62, the intermediate shaft 64, and the inner shaft 66 are longitudinally moveable relative to one another. In some embodiments, a user of the delivery system 60 moves the outer sheath 62 in a longitudinal direction with the handle 70.

In at least one embodiment, the lumen 67 of inner shaft 66 is in fluid communication with the lumen of the needle 68 and with the reservoir 72 of inflation media. In some embodiments, to expand the obstructer 40, inflation media flows from the reservoir 72 through the lumen 67 of inner shaft 66, into the lumen of the needle 68, and into the lumen of the obstructer 40. In one embodiment, the reservoir 72 is a syringe.

In some embodiments, the obstructer 40 is in a collapsed state and wrapped around the needle 68, the inner shaft 66, or the needle 68 and the inner shaft 66 for delivery (not shown). The obstructer 40 can be wrapped in any suitable manner, for example in the same manner by which a dilatation balloon is wrapped around a shaft. In at least one embodiment, an obstructer 40 wrapped for delivery is made of a semi-compliant material, a compliant material, and combinations thereof.

In other embodiments, the obstructer 40 is not wrapped for delivery. This is shown for example in FIG. 14. In one embodiment, an obstructer 40 made of a compliant material is not wrapped for delivery.

In at least one embodiment, the valve 10 is positioned within the outer sheath 62 (i.e. in the lumen 63 of the outer sheath 62). Thus, both the valve body 22 and the obstructer 40 are positioned in the lumen 63 of the outer sheath 62. In some embodiments, the obstructer 40 is positioned within the valve body 22, as shown for example in FIG. 14. In other embodiments, the obstructer 40 positioned proximal to the distal end of the valve body 22, as shown for example in FIG. 15.

In at least one embodiment, the valve body 22 is positioned in the lumen 63 of the outer sheath 62 and the obstructer 40 is positioned in the lumen 65 of the intermediate shaft 64, as shown for example in FIG. 15.

In at least one embodiment, a method of delivering a valve 10 includes at least some of the following steps:
 1. collapsing the valve 10 into a collapsed configuration so that both the valve body 22 and the obstructer 40 are in a collapsed state;
   a. wherein the valve 10 is collapsed by crimping;
 2. loading the collapsed valve 10 into a delivery system 60;
 3. removing air from the delivery system 60;
 4. inserting the delivery system 60 into the vascular system;
 5. advancing the delivery system 60 to a desired location in the vascular system;
 6. deploying the valve 10;
   a. wherein deploying includes retracting the outer sheath 62 from the valve 10;
   b. wherein deploying includes pushing the valve 10 out of the open distal end of the outer sheath 62;
     i. wherein pushing the valve 10 includes advancing the push rod 64;
 7. inflating the obstructer 40;
   a. wherein inflating includes injecting expansion media into the obstructer 40;
     i. wherein a needle 68 is used for the inflating step;
 8. withdrawing the needle 68 from the obstructer 40 and into the delivery system 60;
 9. at least partially withdrawing the delivery system 60; and
 10. verifying proper function of the implanted valve 10.

In at least one embodiment, a method of delivering a valve 10 includes at least some of the following steps:
 1. inserting or loading the valve body 22 and obstructer 40 into a delivery system 60, where the valve body 22 and the obstructer 40 are each in a collapsed state;
   a. wherein the obstructer 40 is not within the valve body 22;
     i. wherein the valve body 22 is distal to the obstructer 40;
       a. wherein the valve body 22 and the obstructer 40 are each positioned in the lumen 63 of the outer sheath 62;
       b. wherein the valve body 22 is positioned in the lumen 63 of the outer sheath 62 and the obstructer 40 is positioned in the lumen 65 of the intermediate shaft 64;
     b. wherein the obstructer 40 is wrapped around the inner shaft 66;
       i. wherein the obstructer 40 is made of a semi-compliant material or a non-compliant material;
     c. wherein the obstructer is not wrapped around the inner shaft 66;
       ii. wherein the obstructer 40 is made of a compliant material;
 2. advancing the delivery system 60 through the vasculature system;
 3. deploying the valve body 22 at a desired location in the vasculature system;
   a. wherein deploying includes expanding the valve body 22;
   b. wherein after the valve body 22 is deployed, the valve 10 is in a partially expanded configuration;
 4. deploying the obstructer 40;
   a. wherein deploying includes placing the obstructer 40 into the lumen of the expanded valve body 22;
     i. wherein placing the obstructer 40 in the lumen of the valve body 22 includes advancing the inner shaft 66 until the obstructer 40 is within the lumen of the valve body 22;
     ii. wherein after the obstructer 40 is positioned within the lumen of the valve body 22, the valve 10 is in a partially expanded configuration;
   b. wherein deploying further includes expanding the obstructer 40;
     i. wherein expanding the obstructer 40 includes injecting expansion media into the obstructer 40;
     ii. wherein a needle 68 is used for injecting fluid into the obstructer 40;
     iii. wherein after the obstructer 40 is expanded, the valve 10 is in an expanded configuration
 5. withdrawing the delivery system 60 from the vasculature system;

In at least one embodiment, a method of delivering a valve 10 includes at least some of the following steps:
 1. delivering a valve 10 by a catheter device to a desired location in a body lumen where the valve 10 includes a valve body 22 and an obstructer 40;
   a. wherein the valve 10 is in a collapsed configuration when the valve 10 is being delivered by the catheter device;
 2. expanding the valve body 22; and
   a. wherein the entire valve body 22 is expanded at the same time;
   b. wherein a first portion of the valve body 22 is expanded and then a second portion of the valve body 22 is expanded. For example, in order to seat the valve at the base of the native valve, the proximal end region of the valve body can be expanded first and the rest of the valve body expanded when the valve has the desired position at the native valve;
   c. wherein the valve 10 is in a partially expanded configuration after the valve body 22 is expanded;
 3. expanding the obstructer 40;
   a. wherein the obstructer 40 is expanded by an expansion media delivered to the lumen of the obstructer 40;
   b. wherein the expansion media is delivered to the lumen of the obstructer 40 by a port 42;

i. wherein a needle 68 is inserted through the port 42 into the lumen of the obstructer 40, and the expansion media delivered through the lumen of the needle 68 into the lumen of the obstructer 40;

c. wherein the valve body 22 is in an expanded configuration after the obstructer 40 is expanded.

In at least one embodiment, the valve body 22 has a greater longitudinal length during delivery than the length of the valve body 22 when implanted at the site of a native valve. For example, a valve body made of a shape memory alloy with superelastic properties, can be lengthened for delivery by the application of a stress/load by the delivery system, thereby collapsing the valve body, and upon removal of the load, the valve body returns to its original shape upon implantation at the site of a native valve.

In at least one embodiment, the obstructer 40 of an implanted valve 10 can be replaced. In some embodiments, a method of replacing the obstructer 40 of an implanted valve 10 includes at least some of the following steps:

1. advancing a catheter assembly through the vasculature to the implanted valve 10;
2. puncturing the obstructer 40;
  a. wherein the catheter assembly includes a needle which is used deflate the obstructer 40;
    i. wherein the needle withdraws expansion media from the obstructer 40 to deflate the obstructer 40;
    ii. wherein the needle punctures the obstructer 40 to deflate the obstructer 40;
3. removing the deflated obstructer 40 from the valve 10;
  a. wherein the deflated obstructer proximally withdrawn through a lumen of the catheter assembly;
4. inserting a deflated replacement obstructer 40 into the lumen of the valve body 22;
  a. wherein the replacement obstructer 40 has a port 42;
  b. wherein inserting the obstructer 40 in the lumen of the valve body 22 includes advancing a shaft of the catheter assembly until the obstructer 40 is within the lumen of the valve body 22 where the obstructer is at a distal end of the shaft;
    i. wherein the distal end of the shaft is a needle;
5. expanding the replacement obstructer 40;
  a. wherein the obstructer 40 is expanded by an expansion media delivered to the lumen of the obstructer 40;
  b. wherein the expansion media is delivered to the lumen of the obstructer 40 by a port 42;
    i. wherein a needle extends through the port 42 into the lumen of the obstructer 40, and the expansion media delivered through the lumen of the needle into the lumen of the obstructer 40; and
6. withdrawing the catheter assembly from the vasculature;

The following numbered statements describe the valve 10 disclosed above:

1. A valve having a proximal end and a distal end, the valve comprising:
an expandable valve body extending from the proximal end to the distal end of the valve, the valve body defining a lumen; and
an obstructer retained between the proximal and distal ends of the valve and within the lumen of the valve body when the valve is in an expanded configuration, the obstructer longitudinally moveable within the lumen.

2. A valve having a proximal end and a distal end, the valve comprising:
an expandable valve body extending from the proximal end to the distal end of the valve, the valve body defining a lumen; and
an expandable obstructer;
the valve having an expanded configuration wherein the expandable valve body is in an expanded state and the obstructer is in an expanded state, wherein the obstructer in the expanded state is retained between the proximal and distal ends of the valve and within the lumen of the valve body, the obstructer longitudinally moveable within the lumen.

3. The valve of statement 2, further having a collapsed configuration wherein the expandable valve body is in a collapsed state and the obstructer is in a collapsed state.

4. A valve having a proximal end and a distal end, the valve comprising:
an expandable valve body extending from the proximal end to the distal end of the valve, the valve body comprising an impermeable section and a permeable section;
an obstructer retained between the proximal and distal ends of the valve and within the lumen of the valve body when the valve is in an expanded configuration, the obstructer longitudinally moveable within the lumen.

5. The valve of statements 1 and 4, wherein the obstructer is expandable.

6. The valve of statements 1-5, wherein the obstructer is a balloon.

7. The valve of statements 1-6, the expandable valve body further comprising a first neck region having a reduced inner diameter, the obstructer having a diameter greater than the reduced inner diameter of the first neck region.

8. The valve of statements 7, the first neck region comprising at least one stop affixed to an inner surface of the expandable valve body, the at least one stop defining the reduced inner diameter.

9. The valve of statement 7, the first neck region further having a reduced outer diameter.

10. The valve of statement 7, the expandable valve body further comprising a second neck region having a second neck region diameter, the second neck region a longitudinal distance away from the first neck region, the obstructer having a diameter greater than the second neck region diameter.

11. The valve of statements 1-10, the expandable valve body defining a plurality of side openings between the proximal end and the distal end of the valve, the plurality of side openings comprising:
a plurality of first side openings having a first size; and
a plurality of second side openings having a second size larger than the first size, the second size configured for blood to flow therethrough.

12. The valve of statements 1-11, the expandable valve body being a stent.

13. The valve of statements 1-12, the valve body comprising a plurality of elements and an end, and an end lumen opening, wherein some of the plurality of elements extend inwards at a 90° angle relative to a longitudinal axis of the valve to define the end lumen opening and to form the end of the valve body.

14. The valve of statement 13, wherein the distal ends of the plurality of elements are affixed to one another by an end ring, the end ring defining the distal end lumen opening.

15. The valve of claim 13, the distal end lumen opening defined by the end ring having a first ring diameter, the obstructer having a collapsed diameter, the first ring diameter being greater than the collapsed diameter of the obstructer.

16. The valve of statements 1-12, the valve body being an expandable mesh, the expandable mesh including a plurality of end loops at the distal end of the expandable valve body, the one end of the expandable valve body further comprising an end ring interconnecting the plurality of end loops, the end ring defining an end lumen opening.

17. The valve of claim 16, the distal end lumen opening defined by the end ring having a first ring diameter, the obstructer having a collapsed diameter, the first ring diameter being greater than the collapsed diameter of the obstructer.

18. The valve of statements 1-17, the valve body further comprising an anchor region and a cover affixed to at least one an inner surface and an outer surface of the anchor region.

19. The valve of statement 18, the cover being impermeable.

20. The valve of statement 19, the cover being affixed to the impermeable section of the valve body.

21. The valve of statements 1-20, the valve body being self-expandable or balloon expandable 22. The valve of statement 21, the self-expandable valve body comprising a shape memory alloy.

23. The valve of statement 21, the shape memory alloy having superelastic properties.

24. The valve of statements 1-23, the obstructer made of a biocompatible polymeric material.

25. The valve of statement 24, the biocompatible polymeric material being selected from the group comprising a compliant material, a semi-compliant material, a non-compliant material, and combinations thereof 26. The valve of statements 1-25, the valve further comprising at least one radiopaque area, band, or coating.

27. The valve of statements 1-26, the valve further comprising a therapeutic agent.

28. The valve of statements 1-6, 11-13, and 16-27, the valve body comprising:
a proximal end region;
a distal end region;
wherein the obstructer is longitudinally moveable within the lumen of the distal end region of the valve body.

29. The valve of statement 28, the proximal end region longitudinally adjacent to the distal end region.

30. The valve of statement 28, the proximal end region being an anchor region of the valve.

31. The valve of statements 29-30, the obstructer having a diameter greater than a diameter of the proximal end region.

32. The valve of statements 29-31, the valve body further comprising a first neck region, the first neck region being between the proximal end region and the distal end region.

33. The valve of statements 28-31, the valve body further comprising a second neck region, the second neck region forming an end of the distal end region and forming an end of the valve body.

34. The valve of statement 32, wherein the first neck region is curved and the second neck region is sloped.

35. The valve of statements 28-31, the valve body having a length extending from the proximal end to the distal end of the valve, the valve body comprising a first neck region, the neck first region having a reduced inner diameter, the length of the valve body having a constant outer diameter.

36. The valve of statements 28-35, an end of the valve comprising an end ring defining an end lumen opening, the end lumen opening having a first ring diameter less than a diameter of the end of the valve.

37. The valve of statement 36, the end of the valve further comprising a plurality of elements extending to the end ring.

38. The valve of claim 37, the obstructer having a collapsed diameter, the first ring diameter being greater than the collapsed diameter of the obstructer.

39. The valve of statement 37, the plurality of elements being end loops, the end ring extending through the end loops.

40. The valve of claim 39, the obstructer having a collapsed diameter, the first ring diameter being greater than the collapsed diameter of the obstructer.

41. The valve of statement 37, the plurality of elements affixed to the end ring.

42. The valve of statements 1-6, 11-13, and 16-27, the valve body comprising:
a proximal end region;
a middle region; and
a distal end region;
wherein the obstructer is longitudinally moveable within the lumen of the proximal end region, the middle region, and the distal end region.

43. The valve of statement 42, the proximal end region, the middle region, and the distal end region being longitudinally adjacent to one another with the middle region positioned between the proximal end region and the distal end region.

44. The valve of statement 42, the middle region being an anchor region of the valve.

45. The valve of statements 42-43, the proximal end region including a neck region and the distal end region including a neck region.

46. The valve of statement 45, the proximal end region being an anchor region of the valve.

47. The valve of statement 46, the proximal end region including a neck region, the neck region having a reduced inner diameter, the length of the valve body having a constant outer diameter.

48. The valve of statement 47, the distal end region including a neck region having a reduced diameter.

49. The valve of statement 46, the proximal end region having a first maximum outer diameter, the middle region having a second maximum outer diameter, and the distal end region having a third maximum outer diameter, the second maximum outer diameter being greater than the first maximum outer diameter and the third maximum outer diameter.

50. The valve of statement 49, the middle region having a first neck region and a second neck region.

51. The valve of statements 42-50, an end of the valve comprising an end ring defining an end lumen opening, the end lumen opening having a first ring diameter less than a diameter of the end of the valve.

52. The valve of statement 51, the end of the valve further comprising a plurality of elements extending to the end ring.

53. The valve of claim 52, the obstructer having a collapsed diameter, the first ring diameter being greater than the collapsed diameter of the obstructer.

54. The valve of statement 52, the plurality of elements being end loops, the end ring extending through the end loops.

55. The valve of claim 54, the obstructer having a collapsed diameter, the first ring diameter being greater than the collapsed diameter of the obstructer.

56. The valve of statement 3 in combination with a catheter, the valve being in the collapsed configuration, the catheter comprising:
a tubular outer sheath defining an outer lumen;
a tubular intermediate shaft defining an intermediate lumen, the tubular intermediate shaft positioned within the outer lumen; and
a tubular inner shaft defining an inner lumen, the inner shaft positioned within the intermediate lumen;
the outer sheath, the intermediate shaft, and the inner shaft being longitudinally moveable relative to one another;
wherein the valve body is positioned within the outer lumen and the obstructer is releasably engaged to the tubular inner shaft.

57. The valve of statement 56, wherein the obstructer is positioned within the lumen of the expandable valve body, the tubular inner shaft extending through an end lumen opening defined by the expandable valve body.

58. The valve of statement 56, wherein the obstructer is proximal to the expandable valve body.

59. The valve of statement 56-58, wherein the obstructer is wrapped around the needle.

60. The valve of statement 59, wherein the obstructer comprises a semi-compliant material, a compliant material, and combinations thereof 61. A valve system comprising:
a valve having a proximal end and a distal end, the valve being in an collapsed configuration, the valve comprising:
an expandable valve body extending from the proximal end to the distal end of the valve, the valve body defining a lumen; and
an obstructer;
a catheter comprising:
a tubular outer sheath defining an outer lumen;
a tubular intermediate shaft defining an intermediate lumen, the tubular intermediate shaft positioned within the outer lumen; and
a tubular inner shaft defining an inner lumen, the inner shaft positioned within the intermediate lumen;
the outer sheath, the intermediate shaft, and the inner shaft being longitudinally moveable relative to one another;
wherein the expandable valve body is positioned within the outer lumen and the obstructer is releasably engaged to the tubular inner shaft.

62. The valve of statement 61, wherein the obstructer is positioned within the lumen of the expandable valve body, the tubular inner shaft extending through an end lumen opening defined by the expandable valve body.

63. The valve of statement 61, wherein the obstructer is proximal to the expandable valve body.

64. The valve of statement 63, wherein the obstructer is positioned within either the outer lumen or the intermediate lumen.

65. The valve of statement 61-64, wherein the obstructer is wrapped around the needle.

66. The valve of statement 65, wherein the obstructer comprises a semi-compliant material, a compliant material, and combinations thereof 67. The valve system of claim 61, wherein the expandable valve body is as described in one or more of statements 4, 7-16, 18-23, 28-30, 32-37, 39, 41-52, 54, and combinations thereof 68. The valve system of statements 60-67 wherein the obstructer is described in one or more of statements 5-6, 15-17, 24-25, 31, 38, 40, 53, 55 and combinations thereof 69. The valve system of statements 60-68, wherein the valve further includes a cover as described in statement 18-20; a radiopaque marker as described in statement 26; a therapeutic agent as described in statement 27; and combinations thereof.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A valve having a proximal end and a distal end, the valve comprising:
an expandable valve body extending from the proximal end to the distal end of the valve, the valve body defining a lumen; and
an obstructer retained between the proximal and distal ends of the valve and within the lumen of the valve body when the valve is in an expanded configuration, the obstructer longitudinally moveable within the lumen;
the valve body being an expandable mesh, the expandable mesh including end loops at the distal end of the expandable valve body, the one end of the expandable valve body further comprising an end ring interconnecting the end loops, the end ring defining an end lumen opening.

2. The valve of claim 1, wherein the obstructer is expandable.

3. The valve of claim 2, wherein the obstructer is a balloon.

4. The valve of claim 1, the expandable valve body further comprising a first neck region having a reduced inner diameter, the obstructer having a diameter greater than the reduced inner diameter of the first neck region.

5. The valve of claim 4, the first neck region comprising at least one stop affixed to an inner surface of the expandable valve body, the at least one stop defining the reduced inner diameter.

6. The valve of claim 4, the first neck region further having a reduced outer diameter.

7. The valve of claim 4, the expandable valve body further comprising a second neck region having a second neck region diameter, the second neck region a longitudinal distance away from the first neck region, the obstructer having a diameter greater than the second neck region diameter.

8. The valve of claim 1, the expandable valve body defining a plurality of side openings between the proximal end and the distal end of the valve, the plurality of side openings comprising:
a plurality of first side openings having a first size; and
a plurality of second side openings having a second size larger than the first size, the second size configured for blood to flow therethrough.

9. The valve of claim 1, the expandable valve body being a stent.

10. The valve of claim 1, wherein the end loops extend inwards at a 90° angle relative to a longitudinal axis of the valve.

11. The valve of claim 1, the valve body further comprising an anchor region and a cover affixed to at least one an inner surface and an outer surface of the anchor region.

12. The valve of claim 1, wherein the end loops are elongated.

13. A valve having a proximal end and a distal end, the valve comprising:
   an expandable valve body extending from the proximal end to the distal end of the valve, the valve body defining a lumen; and
   an expandable obstructer;
   the valve having an expanded configuration wherein the expandable valve body is in an expanded state and the obstructer is in an expanded state, wherein the obstructer in the expanded state is retained between the proximal and distal ends of the valve and within the lumen of the valve body, the obstructer longitudinally moveable within the lumen;
   the valve having a collapsed configuration wherein the expandable valve body is in a collapsed state and the obstructer is in a collapsed state;
   the valve in combination with a catheter, the valve being in the collapsed configuration, the catheter comprising:
      a tubular outer sheath defining an outer lumen;
      a tubular intermediate shaft defining an intermediate lumen, the tubular intermediate shaft positioned within the outer lumen; and
      a tubular inner shaft defining an inner lumen, the inner shaft positioned within the intermediate lumen;
      the outer sheath, the intermediate shaft, and the inner shaft being longitudinally moveable relative to one another;
   wherein the valve body is positioned within the outer lumen and the obstructer is releasably engaged to the tubular inner shaft and the obstructer is proximal to the expandable valve body.

14. The valve of claim 13, the inner shaft having needle at a distal end, wherein the obstructer is wrapped around the needle.

15. A valve system comprising:
   a valve having a proximal end and a distal end, the valve being in an collapsed configuration, the valve comprising:
      an expandable valve body extending from the proximal end to the distal end of the valve, the valve body defining a lumen; and
      an obstructer;
   a catheter comprising:
      a tubular outer sheath defining an outer lumen;
      a tubular intermediate shaft defining an intermediate lumen, the tubular intermediate shaft positioned within the outer lumen; and
      a tubular inner shaft defining an inner lumen, the inner shaft positioned within the intermediate lumen;
      the outer sheath, the intermediate shaft, and the inner shaft being longitudinally moveable relative to one another;
   wherein the expandable valve body is positioned within the outer lumen and the obstructer is releasably engaged to the tubular inner shaft.

16. The valve system of claim 15, wherein the obstructer is positioned within the lumen of the expandable valve body, the tubular inner shaft extending through an end lumen opening defined by the expandable valve body.

17. The valve system of claim 15, wherein the obstructer is positioned in the intermediate lumen.

18. The valve system of claim 15, wherein the obstructer is wrapped for delivery.

* * * * *